(12) United States Patent
Macia Barber et al.

(10) Patent No.: US 10,542,935 B2
(45) Date of Patent: *Jan. 28, 2020

(54) SENSORS

(71) Applicant: Smart Solutions Technologies, S.L., Madrid (ES)

(72) Inventors: Agustin Macia Barber, Torrelodones (ES); Daniel Llorca Juan, Porto San Giorgio (IT); Christian Vicente Rengel, Paiporta (ES); Borja Gonzalvez Munoz, Las Matas (ES)

(73) Assignee: Smart Solutions Technologies, S.L., Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 16/281,032

(22) Filed: Feb. 20, 2019

(65) Prior Publication Data

US 2019/0183421 A1    Jun. 20, 2019

Related U.S. Application Data

(63) Continuation of application No. 15/640,360, filed on Jun. 30, 2017, now Pat. No. 10,238,336, which is a (Continued)

(30) Foreign Application Priority Data

| Nov. 17, 2010 | (EP) | ................................. 2010191590 |
| Apr. 12, 2011 | (EP) | ................................. 2011162135 |
| Jun. 26, 2012 | (EP) | ................................. 2012174367 |

(51) Int. Cl.
*A61B 5/04*     (2006.01)
*A61B 5/00*     (2006.01)
(Continued)

(52) U.S. Cl.
CPC ........ *A61B 5/6804* (2013.01); *A61B 5/02055* (2013.01); *A61B 5/04085* (2013.01);
(Continued)

(58) Field of Classification Search
CPC . A61B 5/04085; A61B 5/6804; A61B 5/0006; A61B 5/0402; A61B 5/0452;
(Continued)

(56) References Cited

U.S. PATENT DOCUMENTS

| 3,954,100 A | 5/1976 | Sem-Jacobsen |
| 3,993,049 A | 11/1976 | Kater |

(Continued)

FOREIGN PATENT DOCUMENTS

| CN | 1732029 A | 2/2006 |
| EP | 0788811 A1 | 8/1997 |

(Continued)

OTHER PUBLICATIONS

Carpi et al. "Electroactive Polymer-Based Devices for e-Textiles in Biomedicine" IEEE Transactions on Information Technology in Biomedicine 9(3): 295-318 (2005).

(Continued)

*Primary Examiner* — Joseph A Stoklosa
*Assistant Examiner* — Brian M Antiskay
(74) *Attorney, Agent, or Firm* — Entralta P.C.; Justin G. Sanders; Peter D. Weinstein

(57) ABSTRACT

A sensor is disclosed comprising, in at least one embodiment an electrode, a track and an electrical connector, wherein, the track is comprising an electrically conductive flexible and elastic material that comprises an electrically conductive material that is non-contiguous that when stretched is able to transmit an electrical signal from an electrode to an electrical connector and from an electrical connector to an electrode.

20 Claims, 17 Drawing Sheets

Related U.S. Application Data continuation of application No. 13/931,666, filed on Jun. 28, 2013, now Pat. No. 9,808,196, which is a continuation-in-part of application No. 13/988,007, filed as application No. PCT/EP2011/070296 on Nov. 16, 2011, now Pat. No. 9,629,584, said application No. 13/931,666 is a continuation-in-part of application No. PCT/EP2012/056573, filed on Apr. 11, 2012.

(60) Provisional application No. 61/427,864, filed on Dec. 29, 2010, provisional application No. 61/474,484, filed on Apr. 12, 2011, provisional application No. 61/666,623, filed on Jun. 29, 2012.

(51) Int. Cl.

| | | |
|---|---|---|
| *A61B 5/0408* | (2006.01) | |
| *A61B 5/0205* | (2006.01) | |
| *A61B 5/0245* | (2006.01) | |
| *A61B 5/0492* | (2006.01) | |
| *A61B 5/053* | (2006.01) | |
| *A61B 5/08* | (2006.01) | |

(52) U.S. Cl.
CPC .......... *A61B 5/6805* (2013.01); *A61B 5/0245* (2013.01); *A61B 5/0492* (2013.01); *A61B 5/0531* (2013.01); *A61B 5/0816* (2013.01); *A61B 5/4266* (2013.01)

(58) Field of Classification Search
CPC ..... A61B 5/6805; A61B 5/6831; A61B 5/742; A61B 5/6833; A61N 1/0484; A61N 1/04; A61N 1/0476; A61N 1/0492
USPC ................ 600/372, 382, 384, 386, 388–393, 600/508–509
See application file for complete search history.

(56) References Cited

U.S. PATENT DOCUMENTS

| | | | |
|---|---|---|---|
| 4,082,087 | A | 4/1978 | Howson |
| 4,664,118 | A | 5/1987 | Batters |
| 4,708,149 | A | 11/1987 | Axelgaard et al. |
| 4,867,166 | A | 9/1989 | Axelgaard et al. |
| 4,898,689 | A | 2/1990 | Hamada et al. |
| 4,941,961 | A | 7/1990 | Noguchi et al. |
| 5,164,443 | A | 11/1992 | Watanabe |
| 5,289,822 | A | 3/1994 | Highe et al. |
| 5,352,315 | A | 10/1994 | Carrier et al. |
| 5,427,096 | A | 6/1995 | Bogusiewicz et al. |
| 5,746,207 | A | 5/1998 | McLaughlin et al. |
| 5,947,897 | A | 9/1999 | Otake |
| 6,270,466 | B1 | 8/2001 | Weinstein et al. |
| 6,419,636 | B1 | 7/2002 | Young et al. |
| 6,745,082 | B2 | 6/2004 | Axelgaard |
| 7,173,437 | B2 | 2/2007 | Hervieux et al. |
| 7,324,841 | B2 | 1/2008 | Reho et al. |
| 7,502,643 | B2 | 3/2009 | Farringdon et al. |
| 7,522,951 | B2 | 4/2009 | Gough et al. |
| 7,779,656 | B2 | 8/2010 | Dias et al. |
| 7,783,334 | B2 | 8/2010 | Nam et al. |
| 8,112,140 | B2 | 2/2012 | Grabetal |
| 8,369,936 | B2 | 2/2013 | Farringdon et al. |
| 8,700,118 | B2 | 4/2014 | Oster et al. |
| 8,818,478 | B2 | 8/2014 | Scheffler et al. |
| 2003/0163035 | A1 | 8/2003 | Van Heerden et al. |
| 2005/0177059 | A1 | 8/2005 | Koivumaa et al. |
| 2006/0094948 | A1 | 5/2006 | Gough et al. |
| 2006/0095001 | A1 | 5/2006 | Matsumura et al. |
| 2006/0183990 | A1 | 8/2006 | Tolvanen |
| 2007/0060859 | A1 | 3/2007 | Kanamura et al. |
| 2007/0127187 | A1 | 6/2007 | DeFusco et al. |
| 2008/0242176 | A1 | 10/2008 | Jaeger et al. |
| 2008/0287769 | A1 | 11/2008 | Kurzweil et al. |
| 2009/0043185 | A1 | 2/2009 | McAdams et al. |
| 2009/0100566 | A1 | 4/2009 | Schiavino et al. |
| 2009/0282671 | A1 | 11/2009 | Tao et al. |
| 2010/0070007 | A1 | 3/2010 | Parker et al. |
| 2010/0185076 | A1 | 7/2010 | Jeong et al. |
| 2010/0198038 | A1 | 8/2010 | Nagata et al. |
| 2010/0198043 | A1 | 8/2010 | Holzer et al. |
| 2010/0234715 | A1 | 9/2010 | Shin et al. |
| 2011/0230749 | A1 | 9/2011 | Chan et al. |
| 2011/0259638 | A1 | 10/2011 | Sherrill et al. |
| 2012/0246795 | A1 | 10/2012 | Scheffler et al. |

FOREIGN PATENT DOCUMENTS

| | | |
|---|---|---|
| EP | 1361819 B1 | 11/2003 |
| EP | 2072009 A1 | 6/2009 |
| EP | 2196142 A1 | 6/2010 |
| JP | S55-108455 A | 8/1980 |
| JP | 2001-234070 A | 8/2001 |
| JP | 2006-512128 A | 4/2006 |
| JP | 2008-536542 A | 9/2008 |
| KR | 10-0863064 B1 | 10/2008 |
| RU | 2237303 C2 | 9/2004 |
| RU | 55241 U1 | 7/2006 |
| WO | 1997018450 A1 | 5/1997 |
| WO | 2001002052 A2 | 11/2001 |
| WO | 2002030279 A1 | 4/2002 |
| WO | 2002039894 A1 | 5/2002 |
| WO | 2002071935 A1 | 9/2002 |
| WO | 2004058346 A1 | 7/2004 |
| WO | 2004110192 A1 | 12/2004 |
| WO | 2005088772 A1 | 9/2005 |
| WO | 2006046703 A1 | 5/2006 |
| WO | 2006101748 A3 | 9/2006 |
| WO | 2007050650 A2 | 5/2007 |
| WO | 2009020274 A1 | 2/2009 |
| WO | 2009041496 A1 | 4/2009 |

OTHER PUBLICATIONS

De Rossi et al. "Wearable Technology for Biomechanics: e-Textile or Micromechanical Sensors?" IEEE Engineering in Medicine and Biology Magazine, 29: 37-43 (2010).
EPO Extended European Search Report, EP 10191590.8, dated Apr. 28, 2011.
EPO Extended European Search Report, EP 12174367.8, dated Oct. 1, 2012.
EPO Extended European Search Report, EP 16194210.7, dated Mar. 3, 2017.
Franta "Elastomers and Rubber Compounding Materials" Studies in Polymer Science 1, Elsevier, 1989, p. 241.
International Search Report and Written Opinion, PCT/EP2011/070296 dated Feb. 6, 2012.
International Search Report and Written Opinion, PCT/EP2012/056573 dated Sep. 28, 2012.
International Search Report, PCT/EP2013/063881, dated Sep. 20, 2013.
Polar WearLink® + Coded Transmitter 31 Coded Transmitter W.I.N.D. User Manual.
Saleem et al. "Fabrication of Extrinsically Conductive Silicone Rubbers with High Elasticity and Analysis of Their Mechanical and Electrical Characteristics" Polymers 2010, 2, 200-210; doi:10.3390/polym2030200 (2010).
The State Intellectual Property Office of the People's Republic of China Search Report, Application No. 201380044523X, dated Oct. 20, 2015, English Translation.

SENSORS

RELATED APPLICATIONS

This is a continuation application and so claims the benefit pursuant to 35 U.S.C. § 120 of a prior filed and co-pending U.S. non-provisional application Ser. No. 15/640,360, filed on Jun. 30, 2017, which is a continuation application that claims priority pursuant to 35 U.S.C. § 120 to U.S. non-provisional application Ser. No. 13/931,666, filed on Jun. 28, 2013, which is a continuation-in-part application that claims priority pursuant to 35 U.S.C. § 120 to U.S. non-provisional application Ser. No. 13/988,007 (now U.S. Pat. No. 9,629,584), filed on May 16, 2013, a 35 U.S.C. § 371 U.S. national stage application of international patent application serial number PCT/EP2011/070296, filed on Nov. 16, 2011, which claims priority pursuant to 35 U.S.C. § 119(a) to EP patent application serial number 2010191590.8, filed on Nov. 17, 2010, and claims priority pursuant to 35 U.S.C. § 119(e) to U.S. provisional patent application Ser. No. 61/427,864, filed on Dec. 29, 2010. Application Ser. No. 13/931,666 is also a bypass continuation-in-part that claims priority to international patent application serial number PCT/EP2012/056573, filed on Apr. 11, 2012, which claims priority pursuant to 35 U.S.C. § 119(a) to EP patent application serial number 2011162135.5, filed on Apr. 12, 2011, and claims priority pursuant to 35 U.S.C. § 119(e) to U.S. provisional patent application Ser. No. 61/474,484, filed on Apr. 12, 2011. Application Ser. No. 13/931,666 also claims priority pursuant to 35 U.S.C. § 119(a) to EP patent application serial number 2012174367.8, filed on Jun. 29, 2012, and also claims priority pursuant to 35 U.S.C. § 119(e) to U.S. provisional patent application Ser. No. 61/666,623, filed on Jun. 29, 2012, each of which is hereby incorporated by reference in its entirety.

BACKGROUND

Sensors comprising electrodes, a track and an electrical connector are used extensively in the assessment of clinical condition, for example, without limitation, in the monitoring of a cardiac condition. The electrodes are placed in contact with the skin of an individual, including, without limitation, a human body and the electrical physiological signals which result are examined. The physiological signals themselves are transported through an electrically conductive track to an electrical connector which couples with an electronic instrument for receiving, collecting, storing, processing and/or transmitting the data generated by a sensor. Such data may be used to monitor and/or evaluate the health and/or physical state of a wearer.

While using a sensor can provide an accurate measurement of a signal, there are several factors that can affect the signal quality, including, without limitation, stability, noise and/or sensibility. These limitations are due, at least in part, to factors such as motion. This can be exacerbated when a sensor is included in a garment. In such a situation, the electrode and track of a sensor need to be integrated in a garment in a minimally invasive manner that allows, for example, without limitation, flexiblity, and comfort to an individual's body, including in movement and be resistant to degredation due to repeated washing. At the same time, a sensor must also be capable of measuring a signal accurately.

To reduce background noise, one solution has been to attach a sensor to the skin with an adhesive. An issue with such an arrangement has been the lack of comfort and the inability to reuse the sensor as it can only be applied once to an individual at which point it is usually disposed. Therefore, there is a need for a sensor that is integrated in a fabric, such as, without limitation, a garment, wherein an adhesive is eliminated and is replaced with a sensor that is applied to the skin of an individual using the fabric's pressure to the body. One way in which pressure can be created is to make a sensor flexible, elastic and with improved adhesion properties, but avoiding adhesive elements, so that it can adapt to every different type of body. This includes making the track flexible and elastic and the electrode flexible and with improved anti-slip property such that every movement made by an individual's body will be translated into an electrode and a track keeping it in place, while an individual is in motion while retaining the fidelity of the signal. To accomplish this result, a track can be constructed of a flexible and elastic conductive material, for example, without limitation, a silicone conductive rubber.

A problem facing the developers of advanced electronic textiles is how to interconnect electrical components and electronic devices with each other and with electrical connectors via electrically conductive tracks provided on the fabric substrate of an electronic garment. It is known in the field of electronic fabrics, when the substrate is a wearable, elastic and flexible garment, the integration of rigid elements creates a weakness and frequently the rigid element will break the garment when it is stretched.

With regard to a silicone conductive rubber, one issue related to the use of this material in a garment is that the garment can be damaged during the curing process. This has limited the use of silicone conductive rubber as a means to connect an electrode to an electronic connector until a means to cure it on a fabric at room. Other drawbacks of a sensor where the track is made by a semi-conductive elastic material include having a mechanically weak linkage between the track and an electrical connector when the fabric is stretched. One result is that the fabric can tear after suffering a physical stress.

The development of a sensor and a garment comprising a sensor with flexibility and elasticity which allows recording physiological signals, especially in movement, with improved adhesion properties but avoiding adhesive elements which produce skin irritations is of great interest. In addition, the development of an improved silicone conductive elastic track and electrical connector assembly in wearable fabric and a method to cure a silicone conductive rubber at room temperature, including, without limitation, on a garment, is of great interest.

SUMMARY

The present invention solves the problems described above by providing a sensor comprising, in at least one embodiment an electrode, a track and an electrical connector, wherein, the track is comprising an electrically conductive flexible and elastic material that comprises an electrically conductive material that is non-contiguous that when stretched is able to transmit an electrical signal from an electrode to an electrical connector and from an electrical connector to an electrode.

BRIEF DESCRIPTION OF THE DRAWINGS

The accompanying drawings illustrate aspects of the present invention. In such drawings.

DETAILED DESCRIPTION

Figure 1A:
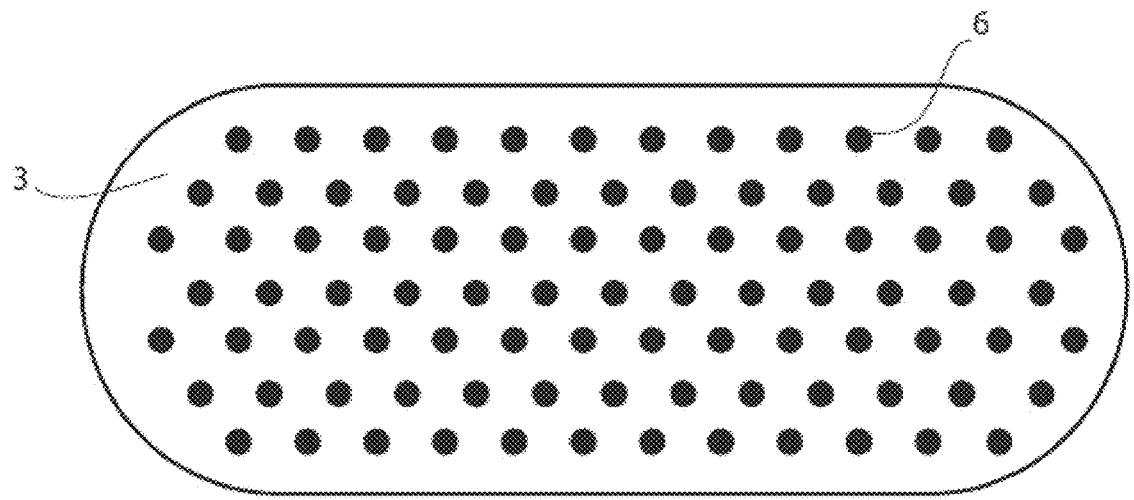
FIG. 1A illustrates an orifices 6 pattern in the electrode 3.

The present invention relates in an embodiment to a sensor comprising an electrode, a track and an electrical connector. The present invention further relates in an embodiment to a fabric that includes a sensor, including without limitation, a fabric that is part of a garment. The present invention also relates in an embodiment to a sensor wherein a track is flexible, elastic and semi-conductive or conductive. The present invention also relates in an embodiment to a sensor with improved anti-slip property wherein an electrode is flexible and comprises a plurality of orifices or grooves in a predefined pattern, filled with silicone rubber.

The present invention also relates in an embodiment to a sensor attached to a fabric comprising at least an elastic and electrically conductive area integrated into the fabric, a process to obtain the fabric, as well as to the use of an elastic conductive material, including, without limitation, silicone rubber, loaded with an electrically conductive material, for the preparation of the fabric of the invention. It also relates in an embodiment, to a sensor comprising the fabric, as well as a garment comprising the sensor. In an embodiment, the present invention can be used, without limitation, to monitor an individual who is undergoing physical activity in a continuous and non-invasive manner.

The term "sensor," without limitation, refers to a component that receives physiological signals and transforms them into electrical signals and is comprising, without limitation, an electrode, a track and an electrical connector.

The term "electrode," without limitation, refers to the area of the conductive layer that is in contact with the skin and wherein the physiological signal is received from or an electrical impulse is transmitted to an individual.

The term "track," without limitation, refers to the area of the conductive layer where the electrical connector is located and connects the electrode to the electrical connector (also hereinafter referred to as the electrically conductive area). The track transmits a physiological signal from an electrode area to an electrical connector or from an electrical connector to an electrode.

The term "carbon black," without limitation, refers to carbon in the form of colloidal particles that are produced by incomplete combustion or thermal decomposition of gaseous or liquid hydrocarbons under controlled conditions. Its physical appearance is that of a black, finely divided pellet or powder. There are different types of carbon black in relation with the reaction condition, these are for example furnace black, lamp black, thermal black, acetylene black, channel black.

The term "electrical connector," without limitation, refers to an electromechanical device which provides a separable interface between two electronic subsystems, sensor and electronic instrument.

The term "anti-slip material," without limitation, refers to a material with a material/skin friction coefficient of at least 0.1, at least 0.2, at least 0.3, at least 0.4, at least 0.5, at least 0.6, at least 0.7, at least 0.8, at least 0.9, at least 1.0. In an embodiment, an anti-slip material is silicone rubber or flourosilicone rubber. In an embodiment, a fluorosilicone rubber has a main chain of $CF_2$. In another embodiment, a silicone rubber contains, without limitation a fluorosiloxane dimethylsiloxane copolymer. In another embodiment, a fluorine rubber contains a vinylidenefluoride, a tetrafluoro-ethylene-proyplene, a fluorine-containing nitrile, a fluorine-containing vinylether, a fluorine-containing triazine and/or a fluorine-containing phosphazine.

The term "room temperature," without limitation, refers to a temperature between 15° C. to 30° C. In an embodiment room temperature refers to, without limitation, a temperature of 15° C., 16° C., 17° C., 18° C., 19° C., 20° C., 21° C., 22° C., 23° C., 24° C., 25° C., 26° C., 27° C., 28° C., 29° C. or 30° C.

The term "screen printing," without limitation, refers to a process made using a stencil in which an image or design is printed on a very fine mesh screen and the printable material is squeegeed onto the printing surface through the area of the screen that is not covered by the stencil.

The term a "printed circuit board," without limitation, comprises a conductive wiring system wherein the conductive material is printed on the board and different electrical components can be bonded to the conductive wiring system, further wherein, each set of different electrical components can achieve a different purpose. The term "fabric" should, without limitation, in the context of the present invention, be understood as a material or product manufactured by textile fibres. The fabric may, for example, be manufactured by means of weaving, braiding, knitting or any other known method in the art.

The term "fabric" should, without limitation, in the context of the present invention, be understood as a material or product manufactured by textile fibres. The fabric may, for example, be manufactured by means of weaving, braiding, knitting or any other known method in the art.

The term "hot-melt adhesive" as used herein, without limitation, refers to a thermoplastic, non-structural adhesive that flows when heated and hardens and strengthens as it cools. In an embodiment, a hot-melt adhesive is, without limitation, ethylene-vinyl acetate ("EVA"), ethylene-acrylate, polyolefins ("PO"), polybutene-1, amorphous polyolefin ("APO"), polyamides, polyesters, polyurethanes ("PUR"), thermoplastic polyurethanes ("TPU"), styrene block copolymers ("SBC"), styrene-butadine ("SBS"), styrene-isoprene-styrene ("SIS"), styrene-ethylenebutylene-styrene ("SEBS"), styrene-ethylene/propylene ("SEP"), polycaprolactone, polycarbonates, fluoropolymers, silicone rubbers, thermoplastic elastomers and/or polypyrrole ("PPY").

Figure 1B:
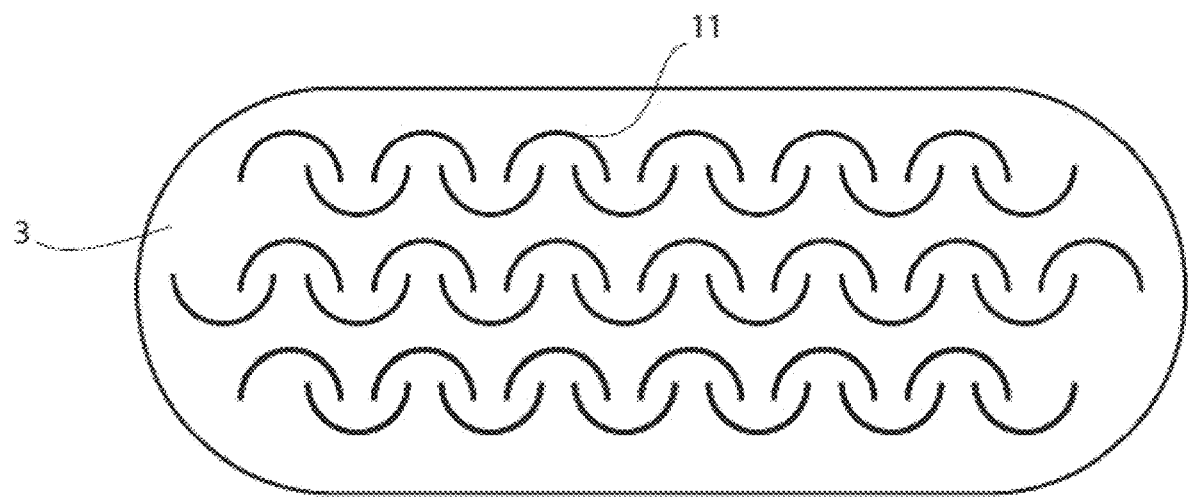
FIG. 1B illustrates a grooves 11 pattern in the electrode 3.
Figure 1C:
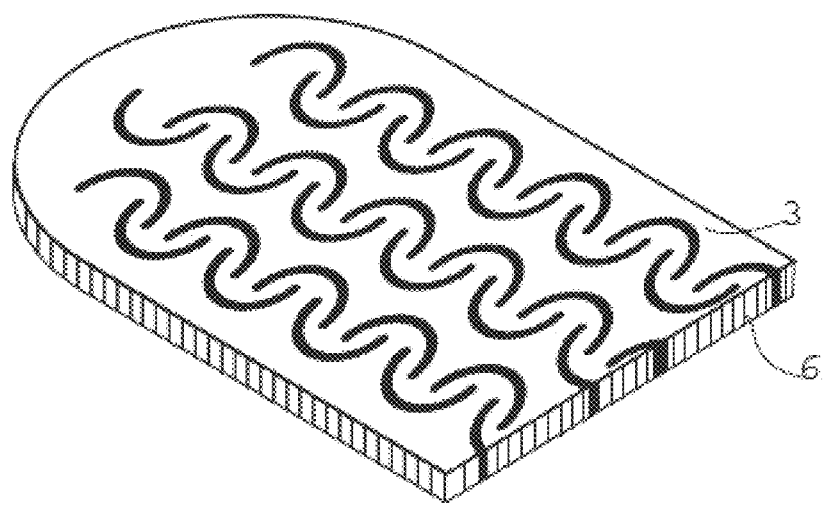
FIG. 1C illustrates an orifices 6 pattern in the electrode 3 with silicone rubber pattern on the surface of the electrode 3.
Figure 1D:
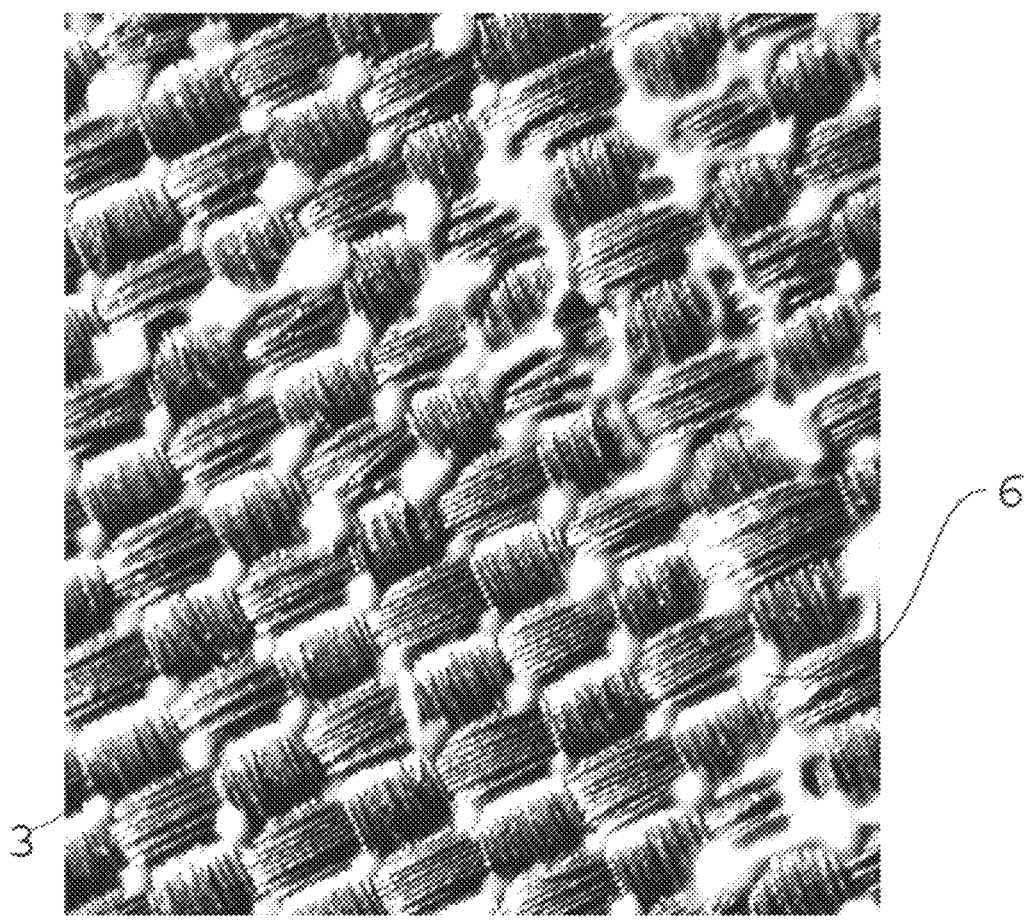
FIG. 1D illustrates a front view of a conductive fabric with the orifices 6 filled with silicone rubber.
Figure 10:
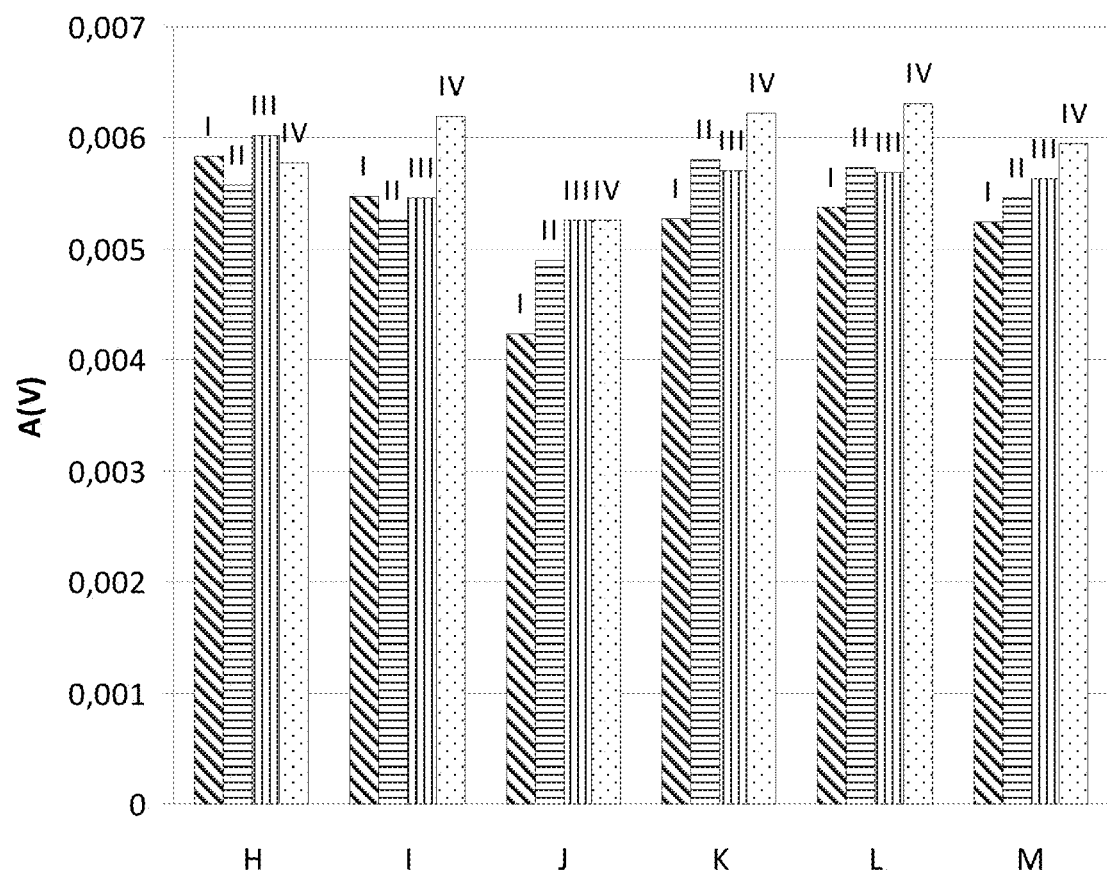
FIG. 10 shows Amplitude RS (A(v)) in mid-speed (H), fast-speed (I), torso-move (J), racket (K), jump (L), and all the activities, mid-speed, fast-speed, torso move, racket and jump (M) for ZEPHYR™ HxM strap (I), Polar TEAM$^2$ strap (II), NUMETREX® Cardio-Shirt (III) and the shirt of the invention (IV).

In an embodiment, the orifices 6 of the electrode 3 as depicted in FIG. 1A show a circular or geometric pattern. In another embodiment, as depicted in FIG. 1B, the orifices show a pattern 11 of grooves in electrode 3. FIG. 10 illustrates electrode 3 with the orifices 6 filled with a flexible non-conductive, semi-conductive or conductive material, including, without limitation, a silicone rubber and/or a fluorosilicone rubber that, without limitation, may include an electrically conductive material, wherein electrode 3 shows the flexible non-conductive, semi-conductive or conductive material, including, without limitation, silicone rubber and/or a fluorosilicone rubber that, without limitation, may include an electrically conductive material, in a predefined pattern on their surface in a relief profile. In an embodiment, the flexible non-conductive, semi-conductive or conductive material, including, without limitation, a silicone rubber and/or a fluorosilicone rubber that, without limitation, may include an electrically conductive material is anchored into the fabric of the electrode, through the filling of the orifices.

In an embodiment, an electrically conductive material is a wire. In another embodiment, an electrically conductive material is comprising a non-contiguous material wherein the material is comprising small molecular structures that individually are too short to reach from an electrode to an electrical connector, but when in a flexible material, for instance, without limitation, silicone rubber and/or fluorosilicone rubber, can be in contact with other small molecular structures that are electrically conductive and allow an electrical signal to pass from an electrode to an electrical connector or from an electrical connector to an electrode.

As depicted in FIGS. 1A-1D, as a result of the interlacing of fibers, the fabric shows a plurality of orifices 6 among fibers. In an embodiment, an electrode is drilled or grooved in order to make additional orifices 6 or grooves 11 or to make the orifices 6 larger and part of a predefined pattern in an electrode. In an embodiment, a plurality of orificies 6 or grooves 11 present different patterns, including, without limitation, circular, sinusoidal, straight lines, hexagon, pentagon, tetragon, triangle, square, diamond and other geometric shapes, or a combination thereof. In another embodiment, the presence of such orifices 6 or grooves 11 in a conductive layer results in an improvement of the elasticity of the layer and, in a further embodiment, by filling a conductive layer orifices 6 or grooves 11 with a flexible material, including, without limitation, a silicone rubber and/or a fluorosilicone rubber, the adherence of a sensor to the skin is improved and the signal measured is improved as the noise of the signal is reduced.

Figure 2:
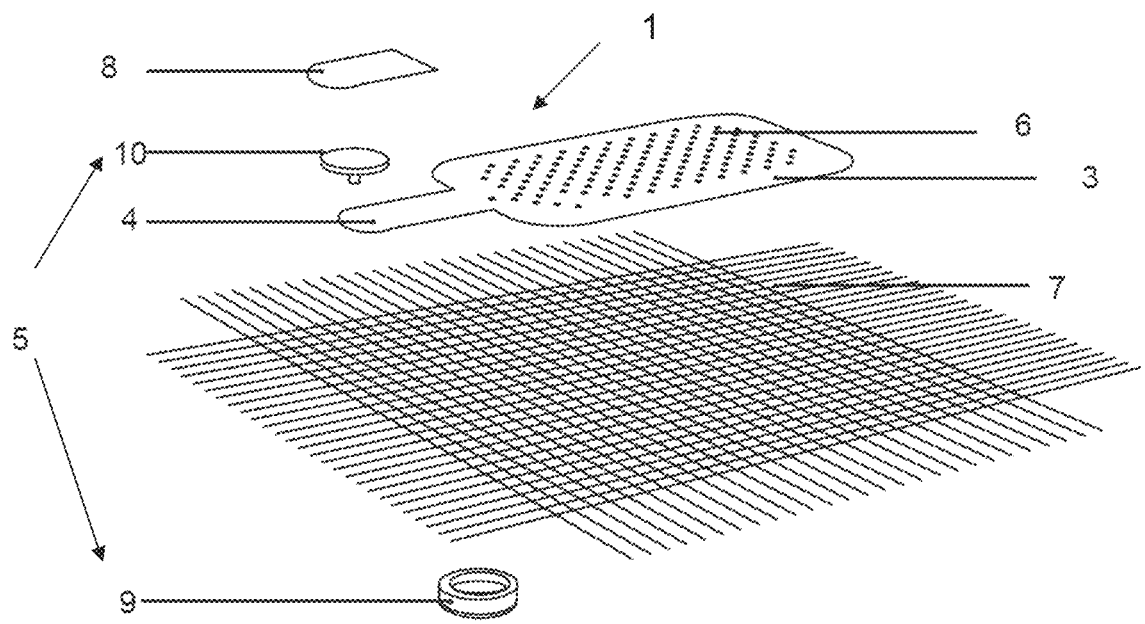
FIG. 2 illustrates exploded perspective view of a sensor according to an embodiment.

FIG. 2 shows an exploded perspective view of a sensor 1 wherein a conductive layer comprises electrode 3 and track 4. In an embodiment, electrode 3 comprises one or more orifices 6 of any shape and size filled with a flexible non-coductive, semi-conductive or conductive material, including, without limitation, silicone rubber and/or fluorosilicone rubber that, without limitation, may include an electrically conductive material. Electrical connector 5 is in contact with track 4 of a conductive layer and track 4 can be covered with insulating material 8. Electrical connector 5 comprises a first and a second portion, wherein the first portion comprise female-type clip portion 9 and the connector second portion may comprise male-type stud portion 10, which portions mate with each other. Electrical connector 5 can, without limitation, include any type of connectors 9 and 10, including where 9 constitutes a male type connector and 10 constitutes a female type connector, which portions mate with each other.

As depicted in FIG. 2, sensor 1 of the present invention allows measuring the electrical physiological signals during physical activity. As mentioned above, a first aspect of the invention relates to sensor 1 to be placed in contact with skin 12 of an individual for acquiring physiological signals which comprises: a) conductive layer 2 comprising at least conductive fibers to be placed in contact with skin 12 for receiving physiological signals; b) electrical connector 5 connected to the conductive layer; characterized in that the conductive layer comprises a plurality of orifices 6 filled with a silicone rubber and/or fluorosilicone rubber throughout the conductive area.

In an embodiment, as depicted in FIG. 2, the conductive layer 2 is made of conductive material, selected from conductive fabric. In another embodiment, it is provided a sensor 1 adapted to be integrated in a garment 7 so as to be placed in contact with skin 12 of a user during the use of the garment 7, wherein said sensor 1 comprises a conductive layer 2 to be placed in contact with the skin 12 for receiving physiological signals comprising at least: an electrode 3; a track 4; and an electrical connector 5 connected with the track 4; wherein the electrode 3 of the conductive layer 2 comprises a plurality of orifices 6 or grooves 11 in a predefined pattern filled with an anti-slip material. In an embodiment, the electrode 3 of the conductive layer 2 comprises a plurality of orifices.

According to an embodiment, electrode 3 and track 4 are made of the same or different material. In an embodiment, electrode 3 and track 4 independently from each other is a conductive fabric comprising a conductive fiber and a non-conductive fiber. In another embodiment, electrode 3 and track 4 refer to a conductive fabric made of a conductive fiber. In another embodiment, electrode 3 and track 4 refer to a conductive fabric made of a conductive fiber and a non-conductive fiber. When orificies 6 or grooves 11 are filled with a flexible, semi-conductive or conductive material, for instance, without limitation, a silicone rubber, such flexible semi-conductive or conductive material presents a flat or relief profile. In an embodiment, without limitation, a silicone rubber and/or a fluorosilicone rubber shows a relief profile. In an embodiment, an electrode is placed in a fabric in such a way that it is electrically in contact with a track.

Figure 3A:
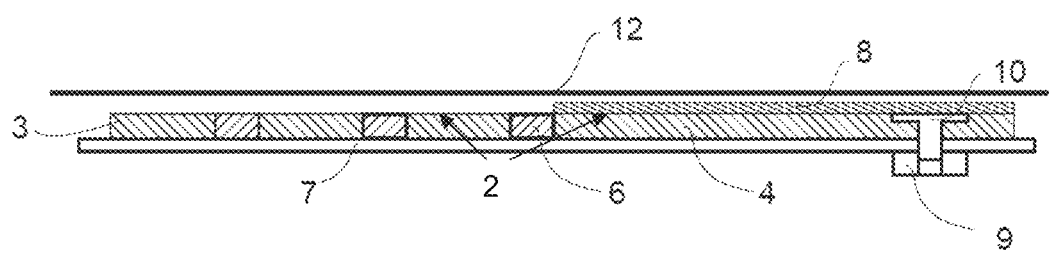
FIG. 3A illustrates a cross-section of a sensor according to an embodiment.

FIG. 3A depicts a cross-section of sensor 1. The cross-section of sensor 1 shows an electrode area 3 and orifice 6 filled with a flexible non-conductive, semi-conductive or a conductive material, including, without limitation, a silicone rubber and/or a fluorosilicone rubber that, without limitation, may include an electrically conductive material. Track 4 is made of the same material as electrode 3. In an embodiment, a track and an electrode are made of a conductive fabric. In an embodiment, a sensor is in contact with skin 12.

Figure 3B:
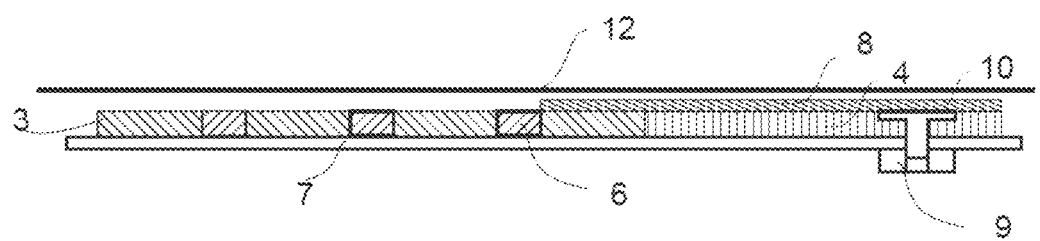
FIG. 3 B illustrates a cross-section of a sensor 1 according to an embodiment.

FIG. 3B depicts a cross-section of an embodiment of a sensor 1. In this embodiment an electrode is made of a conductive fabric and a track 4 is made of a flexible non-conductive, semi-conductive or a conductive material, including, without limitation, silicone rubber and/or a fluorosilicone rubber that, without limitation, may include an electrically conductive material.

As illustrated, FIGS. 3A and 3B may comprise a male and a female portion of an electrical connector that are placed on the opposite face of a garment in juxtaposition with each other. Thus, a male or a female portion which is placed in the inner face, which will be in contact with skin 12 of an individual, is covered with insulating material 8, which also covers track 4 of conductive layer 2. As depicted in FIGS. 3A and 3B, a sensor 1 is integrated in garment 7.

In an embodiment, as depicted in FIGS. 3A and 3B, electrode 2 comprises a conductive fabric made of conductive fibers and non-conductive fibers. In another embodiment, electrode 2 refers to a conductive fabric made of conductive fibers. In an embodiment, a conductive fiber is made of silver coated nylon (such as X-STATIC® yarns from Laird Sauquoit Industries) and a non-conductive fiber is made of nylon. In an embodiment, and without limitation, examples of conductive fibers include fibers made of silver, copper, nickel, stainless steel, gold, non-conductive fibers coated with a conductive material or mixtures thereof. In another embodiment, without limitation, examples of non-conductive fibers include wool, silk, cotton, flax, jute, acrylic fiber, polyamide polyester, nylon and/or with elastic yarns (such as LYCRA® branded spandex from INVISTA™ S.a.r.l).

In an embodiment, the high degree of adhesion strength between a fabric and a flexible, elastic and electrically conductive material, including, without limitation, silicone rubber and/or flurorosilicone rubber including an electrically conductive material is achieved by the coating material penetrating the interstices between the strands anchoring with the structure of the fibers of the fabric, resulting in the integration of the elastic and electrically conductive material into the fabric.

Liquid-printing is a coating method which combines laminating and liquid coating. In an embodiment, this entails, a fabric to be coated with a liquid (low viscosity, medium viscosity or high viscosity) silicone rubber and/or fluorosilicone rubber, wherein, the liquid silicone rubber and/or liquid fluorosilicone rubber is not applied to both sides, but just one side of the fabric in a manner similar to a laminating process. In an embodiment, the thickness of a coating is controlled.

The term liquid-printing encompasses a family of printing processes where the printed material in liquid state is deposited on the support. In an embodiment, liquid-printing processes include, without limitation, screen-printing and digital-printing. In another embodiment, in a digital-printing process, the liquid material is directly applied by a dispenser that reproduces the digitally processed design. In a further embodiment, in a screen-printing process the liquid material is deposited using a stencil. The stencil can be made in different design and thickness.

Figure 4:
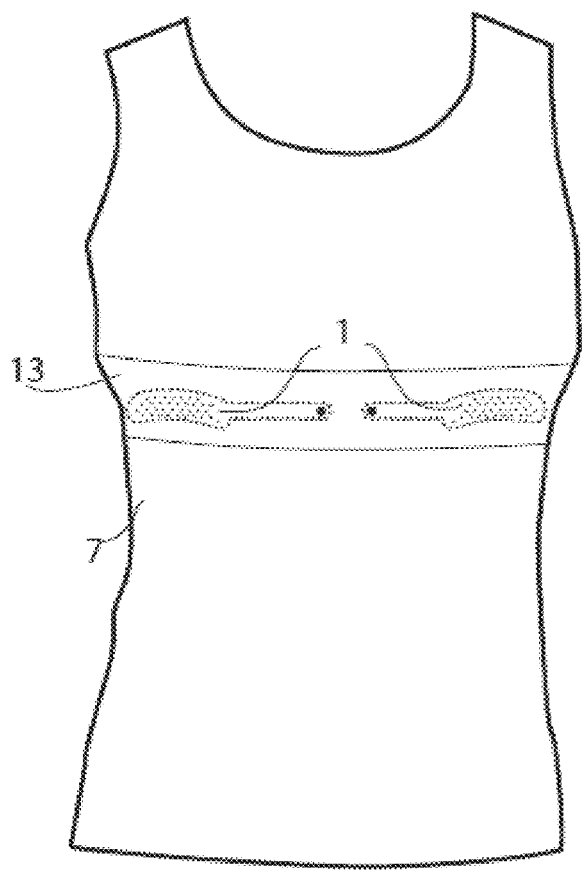
FIG. 4 illustrates elevation view of a garment disclosed herein.

FIG. 4 depicts an elevation view of garment 7 with two sensors 1 placed near the chest area. Outer layer 13 of garment 7 presses sensor 1 with, in an embodiment and without limitation, a sufficient degree of pressure such that sensor 1 is in contact with the skin of a mammal wearing garment 7.

Figure 5:
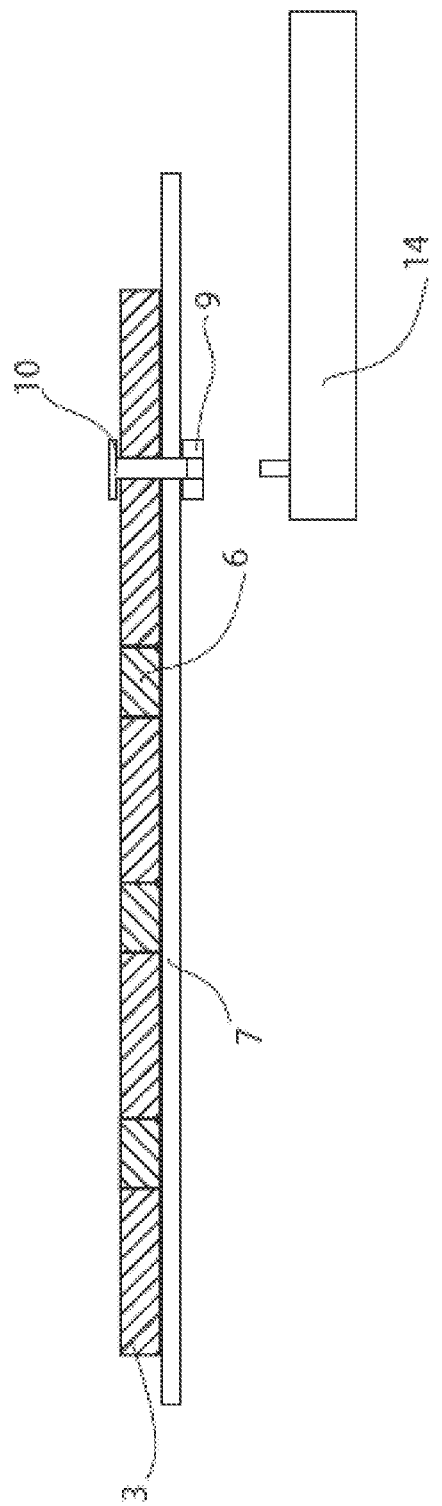
FIG. 5 illustrates cross-section elevation view of a connection between an embodiment of a sensor 1 according to the present invention and an electronic instrument 14.

As depicted in FIGS. 3A, 3B and 4, the use of an electrical connector provided in a sensor and, an electronic instrument may be removably connected to a garment (as depicted in FIG. 5). The electronic instrument may be used for receiving and/or processing and/or sending data from a sensor to a second electronic instrument. The second electronic instrument may be a mobile phone, a PDA, a device capable of displaying a signal received by a sensor and/or a personal computer. In an embodiment, a mobile phone is, without limitation, a smart phone, including, without limitation, an iPhone, an Android phone or a Windows phone. A personal computer, includes, without limitation, a desktop, a laptop, a tablet or a cloud-computing system. Different sensors can be integrated into a wearable fabric, such as for example, without limitation, an electrocardiogram sensor (ECG), an electromyogram sensor (EMG), a galvanic skin response sensor (GSR), an electrochemical sensor, a thermometer, a skin impedance sensor, a transpiration sensor, a respiration sensor, any combination of the aforementioned sensors, or other sensors.

FIG. 5 depicts a cross-section elevation view of a connection between an embodiment of sensor 1 and electronic instrument 14. Sensor 1 is connected, for illustrative purposes only, and without limitation, to electronic connector 5 using female-type clip portion 9 and male-type stud portion 10. Electronic instrument 14 may be directly attached to an electrical connector directly through a coupling, through attachment by a wire between electronic instrument 14 and the electronic connector and/or through a wireless connection.

In an embodiment, a device as depicted in FIG. 5 comprises at least one sensor 1 and an electronic instrument 14 for receiving and collecting and/or storing and/or processing, and/or transmitting data from said sensor. Using the sensor of the invention, the physiological signals detected can be at least one of the following data: cardiac pulse, respiratory frequency, electrodermal response (EDR), measures electrical skin conductivity, electrocardiography (ECG), electromyography (EMG). These signals refer to electrical signals produced in the body.

In an embodiment, a garment is, without limitation, a shirt, a coat, a top, a girdle, underwear, suspenders, a wrist strip, a headband, a belt, a band, a sock, a pair of trousers, a glove, a t-shirt with long sleeves, a t-shirt with short sleeves, a tank top, a leotard, a bra, a sleeveless top, a halter top, a spaghetti-strapped shirt, a singlet, an A-shirt, a tube top and/or any other article that an individual can wear.

In an embodiment, a flexible and/or elastic semi-conductive or conductive material, including, without limitation, a silicone rubber and/or a flourosilicone rubber, has a molecular weight comprised between 400 g/mol and 600 g/mol. In another embodiment, a flexible semi-conductive or conductive material, including, without limitation, a silicone rubber, has a molecular weight of at least 100 g/mol, 200 g/mol, 300 g/mol, 325 g/mol, 350 g/mol, 375 g/mol, 400 g/mol, 425 g/mol, 450 g/mol, 475 g/mol, 500 g/mol, 525 g/mol, 550 g/mol, 575 g/mol, 600 g/mol, 625 g/mol, 650 g/mol, 674 g/mol, 700 g/mol, 800 g/mol, 900 g/mol, 1000 g/mol, or more. In another embodiment, a flexible and/or elastic semi-conductive or conductive material, including, without limitation, a silicone rubber, has a molecular weight of no more than 100 g/mol, 200 g/mol, 300 g/mol, 325 g/mol, 350 g/mol, 375 g/mol, 400 g/mol, 425 g/mol, 450 g/mol, 475 g/mol, 500 g/mol, 525 g/mol, 550 g/mol, 575 g/mol, 600 g/mol, 625 g/mol, 650 g/mol, 674 g/mol, 700 g/mol, 800 g/mol, 900 g/mol or 1000 g/mol.

In a further embodiment, a flexible and/or elastic semi-conductive or conductive material is capable, without limitation, of increasing the stability and reducing the noise and/or sensibility of a signal transferred through a track. In another embodiment, a flexible semi-conductive or conductive material is capable, without limitation, of increasing the stability and reducing the noise and/or sensibility of a signal transferred through a track during periods where the track is stretched, including, without limitation, during use of a garment with a sensor with a flexible track by an individual.

In an embodiment and as described above and as depicted in FIGS. 3A and 3B, sensor 1 is placed in contact with skin 12. In an embodiment, the proportion of conductive layer 2 to be in contact with the skin is comprised between 50% and 80% of the conductive layer and the proportion of a flexible semi-conductive or conductive material, including, without limitation, a silicone rubber, to be in contact with skin 12 is comprised between 20% and 50% in respect to total conductive layer 2. In another embodiment the proportion of conductive layer 2 to be in contact with skin 12 is comprised between 60% and 70% of conductive layer 2 and the proportion of a flexible semi-conductive or conductive material, including, without limitation, a silicone rubber, to be in contact with skin 12 is comprised between 30% and 40% in respect to total conductive layer 2. In another embodiment the proportion of conductive layer 2 to be in contact with skin 12 is comprised between 60% and 70% of the conductive layer 2 and the proportion of a flexible semi-conductive or conductive material, including, without limitation, a silicone rubber, to be in contact with skin 12 is comprised between 30% and 40% in respect to total conductive layer 2.

In an embodiment, the proportion of a conductive layer 2 to be in contact with the skin 12 is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the conductive layer 2. In a further embodiment, the proportion of a conductive layer 2 to be in contact with the skin 12 is no more than 5%, no more than 10%, no more than 15%, no more than 20%, no more than 25%, no more than 30%, no more than 35%, no more than 40%, no more than 45%, no more than 50%, no more than 55%, no more than 60%, no more than 65%, no more than 70%, no more than 75%, no more than 80%, no more than 85%, no more than 90%, no more than 95%, or no more than 100% of the conductive layer 2.

In an embodiment, the proportion of a flexible and/or elastic non-conductive, semi-conductive or conductive material, including, without limitation, a silicone rubber or a fluorosilicone rubber, to be in contact with the skin 12 is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the total conductive layer 2. In an embodiment, the proportion of a flexible and/or elastic non-conductive, semi-conductive or conductive material, including, without limitation, a silicone rubber or a fluorosilicone rubber, to be in contact with the skin 12 is no more than 5%, no more than 10%, no more than 15%, no more than 20%, no more than 25%, no more than 30%, no more than 35%, no more than 40%, no more than 45%, no more than 50%, no more than 55%, no more than 60%, no more than 65%, no more than 70%, no more than 75%, no more than 80%, no more than 85%, no more than 90%, no more than 95%, or no more than 100% of the total conductive layer 2.

In another embodiment, as depicted in FIG. 2, the track 4 and the electric connector 5 are covered with an insulating material 8. In an embodiment, for a sensor in contact with the skin of an individual, the electrode/skin impedance is an element to determine the noise of a signal. In an embodiment, the electrical resistance of a electrode 3 is between 0.5Ω and 10Ω. In a further embodiment the resistance of the track 4 is between 1Ω and 50 kΩ. In another embodiment the resistance of the electrode 3 is at least 0.5Ω, at least 1Ω, at least 2Ω, at least, 3Ω, at least 4Ω, at least 5Ω, at least 6Ω, at least 7Ω, at least 8Ω, at least 9Ω, at least 10Ω, at least 11Ω, at least 12Ω, at least 13Ω, at least 14Ω, at least 15Ω or more. In a further embodiment the resistance of the track 4 is at least 0.5Ω, at least 1Ω, at least 2Ω, at least, 3Ω, at least 4Ω, at least 5Ω, at least 6Ω, at least 7Ω, at least 8Ω, at least 9Ω, at least 10Ω, at least 11Ω, at least 12Ω, at least 13Ω, at least 14Ω, at least 15Ω, at least 16Ω, at least 17Ω, at least 18Ω, at least 19Ω, at least 20Ω, at least 21Ω, at least 22Ω, at least 23Ω, at least 24Ω, at least 25Ω, at least 26Ω, at least 27Ω, at least 28Ω, at least 29Ω, at least 30, at least 31Ω, at least 32Ω, at least 33Ω, at least 34Ω, at least 35Ω, at least 36Ω, at least 37Ω, at least 38Ω, at least 39Ω, at least 40Ω, at least 41Ω, at least 42Ω, at least 43Ω, at least 44Ω, at least 45Ω, at least 46Ω, at least 47Ω, at least 48Ω, at least 49Ω, at least 50Ω, or more.

In another embodiment, as depicted in FIG. 4, a garment 7 includes, without limitation, a sensor 1. In a further embodiment, the garment 7 is designed for applying a pressure equal or higher than 2 KPa. In another embodiment, the garment 7 comprises two layers, an inner and an outer layer 13, and the outer layer 13 compresses the sensor to the body with at least 2 KPa of pressure. In an embodiment, the garment 7 is designed for applying a pressure of at least 1 KPa, at least 1.25 KPa, at least 1.5 KPa, at least 1.75 KPa, at least 2 KPa, at least 3 KPa, at least 4 KPa, at least 5 KPa, at least 6 KPa, at least 7 KPa, at least 8 KPa, at least 9 KPa, at least 10 KPa, at least 11 KPa, at least 12 KPa, at least 13 KPa, at least 14 KPa, at least 15 KPa, at least 16 KPa, at least 17 KPa, at least 18 KPa, at least 19 KPa, at least 20 KPa, at least 21 KPa, at least 22 KPa, at least 23 KPa, at least 24 KPa, at least 25 KPa, at least 26 KPa, at least 27 KPa, at least 28 KPa, at least 29 KPa, at least 30 KPa or more. In another embodiment, the garment 7 comprises two layers, an inner and an outer layer 13, and the outer layer 13 compresses the sensor to the body with at least 1 KPa, at least 1.25 KPa, at least 1.5 KPa, at least 1.75 KPa, at least 2 KPa, at least 3 KPa, at least 4 KPa, at least 5 KPa, at least 6 KPa, at least 7 KPa, at least 8 KPa, at least 9 KPa, at least 10 KPa, at least 11 KPa, at least 12 KPa, at least 13 KPa, at least 14 KPa, at least 15 KPa, at least 16 KPa, at least 17 KPa, at least 18 KPa, at least 19 KPa, at least 20 KPa, at least 21 KPa, at least 22 KPa, at least 23 KPa, at least 24 KPa, at least 25 KPa, at least 26 KPa, at least 27 KPa, at least 28 KPa, at least 29 KPa, at least 30 KPa or more.

In another embodiment, as depicted in FIG. 4, the outer layer 13 comprises a system to regulate the pressure. In a further embodiment, the inner layer has low elasticity and the outer layer 13 has high elasticity. The inner layer is comprising a blend of synthetic fiber and spandex, wherein the synthetic fiber comprises 85% to 90% by weight of the composite elastic material and in a further embodiment, 87% to 89%, and wherein the spandex comprises 10% to 15% by weight of the composite elastic material, and in a further embodiment 11% to 13%. In another embodiment, the outer layer 13 is comprised of a blend of synthetic fiber and spandex, wherein the synthetic fiber comprises 92% to 97% by weight of the composite elastic material and in a further embodiment, 94% to 96%, and wherein the spandex comprises 3% to 8% by weight of the composite elastic material, and in a further embodiment, 4% to 6%. The outer layer 13 compresses the sensor to the skin, and the stability and fixation of the sensor 1 are improved.

In an embodiment, the synthetic fiber comprises at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95% or at least 100% by weight of the composite elastic material. In another embodiment, the spandex comprises at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100% by weight of the composite elastic material.

As depicted in FIGS. 2, 3A, 3B and 4, track 4 of conductive layer 2 of sensor 1 is placed between inner and outer layer 13 of the garment, and electrode 3 is over the inner layer of the garment, electrode 3 being able to be in contact with skin 12 of the user of garment 7. The sensor 1 as depicted in FIG. 2 can be prepared by a process comprising the steps of: a) die cutting a conductive layer of conductive fabric; b) adding a hot melt adhesive on one surface of the conductive layer; c) screen printing with an anti-slip flexible semi-conductive or conductive material, including, without limitation, silicone rubber on the the orificies 6 or grooves 11 of the electrode 3, at a temperature comprise between 10-30° C.; and d) curing the silicone, and in an embodiment, without limitation, for up two minutes at a temperature comprised between 130-190° C. The process can further comprise the step of screen printing with a flexible and/or elastic semi-conductive or conductive material, including, without limitation, silicone rubber loaded with a conductive material to form track 4.

In an embodiment, a first aspect of the invention relates to a fabric which comprises at least an electrically conductive area 1 integrated into the fabric, wherein the electrically conductive area 1 comprises a layer of a flexible semi-conductive or conductive material, including, without limitation, silicone rubber and/or a fluorsilicone rubber loaded with an amount comprising from 5% w/w to 40% w/w of an electrically conductive material. The fabric is able to stretch between 1% and 200% as compared to the same fabric when it is not stretched.

In a further embodiment, a flexible and/or elastic semi-conductive or conductive material, including, without limitation, silicone rubber is loaded with an amount comprising at least 1% w/w, 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w, 15% w/w, 16% w/w, 17% w/w, 18% w/w, 19% w/w, 20% w/w, 21% w/w, 22% w/w, 23% w/w, 24% w/w, 26% w/w, 27% w/w, 28% w/w, 29% w/w, 30% w/w, 31% w/w, 32% w/w, 33% w/w, 34% w/w, 35% w/w, 36% w/w, 37% w/w, 38% w/w, 39% w/w, 40% w/w, 41% w/w, 42% w/w, 43% w/w, 44% w/w, 45% w/w, 46% w/w, 47% w/w, 48% w/w, 49% w/w, 50% w/w, 51% w/w, 52% w/w, 53% w/w, 54% w/w, 55% w/w, 56% w/w, 57% w/w, 58% w/w, 59% w/w, 60% w/w, 65% w/w, 70% w/w, 75% w/w, 80% w/w, 85% w/w, 90% w/w, 95% w/w or more of an electrically conductive material. In another embodiment, a flexible and/or elastic semi-conductive or conductive material, including, without limitation, silicone rubber is loaded with an amount comprising no more than 1% w/w, 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w, 15% w/w, 16% w/w, 17% w/w, 18% w/w, 19% w/w, 20% w/w, 21% w/w, 22% w/w, 23% w/w, 24% w/w, 26% w/w, 27% w/w, 28% w/w, 29% w/w, 30% w/w, 31% w/w, 32% w/w, 33% w/w, 34% w/w, 35% w/w, 36% w/w, 37% w/w, 38% w/w, 39% w/w, 40% w/w, 41% w/w, 42% w/w, 43% w/w, 44% w/w, 45% w/w, 46% w/w, 47% w/w, 48% w/w, 49% w/w, 50% w/w, 51% w/w, 52% w/w, 53% w/w, 54% w/w, 55% w/w, 56% w/w, 57% w/w, 58% w/w, 59% w/w, 60% w/w, 65% w/w, 70% w/w, 75% w/w, 80% w/w, 85% w/w, 90% w/w, 95% w/w or more of an electrically conductive material.

In another embodiment, the fabric is able to stretch at least 1%, at least 2%, at least 3%, at least 4%, at least 5%, 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% at least 100%, at least 105%, at least 110%, at least 115%, at least 120%, at least 125%, at least 130%, at least 135%, at least 140%, at least 145%, at least 150%, at least 155%, at least 160%, at least 165%, at least 170%, at least 175%, at least 180%, at least 185%, at least 190%, at least 195%, at least 200%, at least 210%, at least 220%, at least 230%, at least 240%, at least 250%, at least 260%, at least 270%, at least 280%, at least 290%, at least 300% or more as compared to the same fabric when it is not stretched.

In an embodiment, a fabric that is able to stretch includes, without limitation, an elastic fabric, for example, without limitation, polyester and/or nylon. In a further embodiment, a fabric that is able to stretch is, without limitation, a fabric which comprises a percentage of elastane, from 3% w/w to 20% w/w. In another embodiment, a fabric that is able to stretch is, without limitation, a fabric which comprises a percentage of elastane of at least 1% w/w, 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w, 15% w/w, 16% w/w, 17% w/w, 18% w/w, 19% w/w, 20% w/w, 21% w/w, 22% w/w, 23% w/w, 24% w/w, 26% w/w, 27% w/w, 28% w/w, 29% w/w, 30% w/w, 31% w/w, 32% w/w, 33% w/w, 34% w/w, 35% w/w, 36% w/w, 37% w/w, 38% w/w, 39% w/w, 40% w/w, 41% w/w, 42% w/w, 43% w/w, 44% w/w, 45% w/w, 46% w/w, 47% w/w, 48% w/w, 49% w/w, 50% w/w, 51% w/w, 52% w/w, 53% w/w, 54% w/w, 55% w/w, 56% w/w, 57% w/w, 58% w/w, 59% w/w, 60% w/w, 65% w/w, 70% w/w, 75% w/w, 80% w/w, 85% w/w, 90% w/w, 95% w/w or more. In an embodiment, a fabric that is able to stretch is, without limitation, a fabric which comprises a percentage of elastane of no more than 1% w/w, 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w, 15% w/w, 16% w/w, 17% w/w, 18% w/w, 19% w/w, 20% w/w, 21% w/w, 22% w/w, 23% w/w, 24% w/w, 26% w/w, 27% w/w, 28% w/w, 29% w/w, 30% w/w, 31% w/w, 32% w/w, 33% w/w, 34% w/w, 35% w/w, 36% w/w, 37% w/w, 38% w/w, 39% w/w, 40% w/w, 41% w/w, 42% w/w, 43% w/w, 44% w/w, 45% w/w, 46% w/w, 47% w/w, 48% w/w, 49% w/w, 50% w/w, 51% w/w, 52% w/w, 53% w/w, 54% w/w, 55% w/w, 56% w/w, 57% w/w, 58% w/w, 59% w/w, 60% w/w, 65% w/w, 70% w/w, 75% w/w, 80% w/w, 85% w/w, 90% w/w, 95% w/w or more.

In an embodiment, and as depicted in FIG. 5, electronic instrument 14 that is attached to an electrical connection either directly or through, without limitation a wire, Bluetooth, wireless, RF wireless, other wireless, infrared, laser or optical that is adapted to receive, collect, process, store, and/or transmit data from sensors 1 incorporated in a garment. In an example, data from a sensor 1 comprises an ECG signal that is received by electronic instrument 14. In a further embodiment, different storage, processing, and/or transmitting methods and devices can be incorporated in the electronic instrument.

Figure 15A:
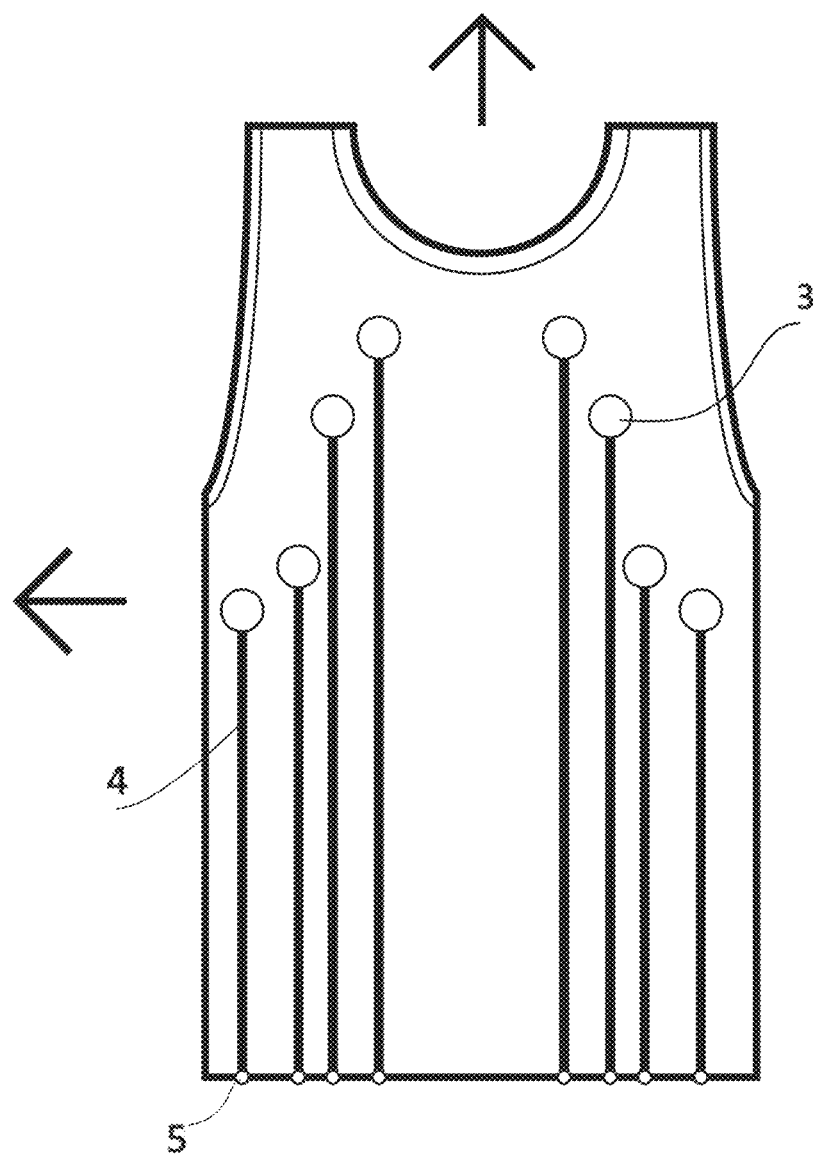
FIG. 15A illustrates elevation view of a garment according to the state of the art.
Figure 15B:
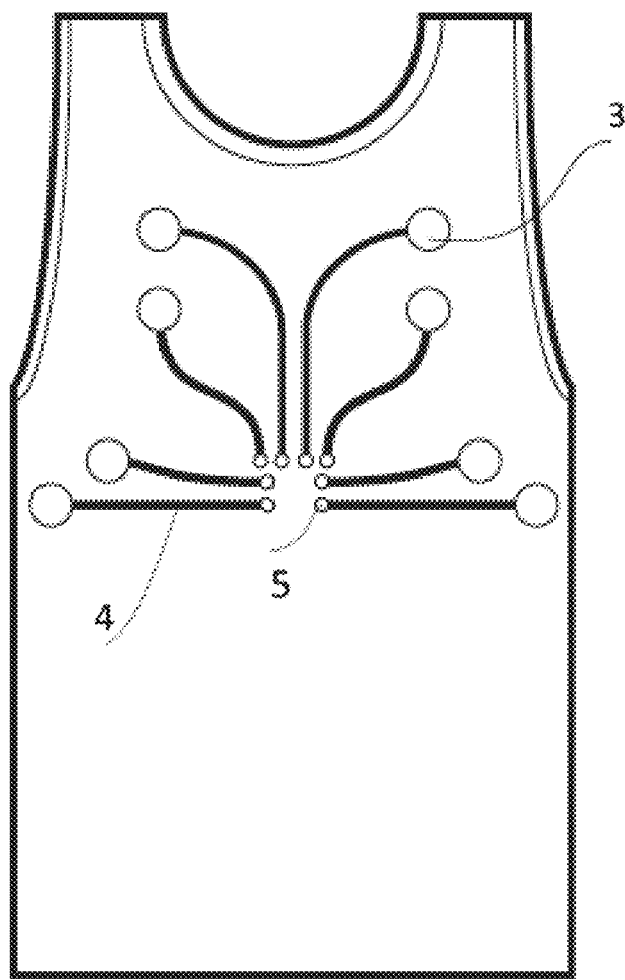
FIG. 15B illustrates elevation view of the garment disclosed herein.

In an embodiment, when the flexible, elastic and electrically conductive area 4 as depicted in FIGS. 15A and 15B is elongated, the fabric support extends substantially the full length of that layer. In another embodiment, the flexibility and the elasticity of a flexible semi-conductive or conductive material, including, without limitation, silicone rubber and/or fluorosilicone rubber enables electrically conductive area 4 to be held in very good conformity and the conductivity is not interrupted.

In an embodiment, electrically conductive area 4 integrated into a fabric may work as a track. In a further embodiment, a fabric comprises at least track 4, at least electrode 3 electrically in contact with track 4, and at least electrical connector 5 placed in track 4. In another embodiment, track 4, transmits an electrical signal from electrode 3 placed in contact with the skin of a user to electrical connector 5 placed in track 4. Connector 5 may be in contact with an electronic instrument for receiving and collecting and/or storing and/or processing, and/or transmitting data from the fabric.

In an embodiment, a flexible and/or elastic semi-conductive or conductive material, including, without limitation, a silicone rubber and/or a fluorosilicone, is in a liquid state prior to the initiation of the process of curing. In another embodiment, a flexible semi-conductive or conductive material, including, without limitation, silicone rubber and/or a fluorosilicone is in a liquid state prior to and/or when it is printed in a fabric. In an embodiment, the adhesion of a flexible and/or elastic semi-conductive or conductive material, including, without limitation, silicone rubber and/or a fluorosilicone in a fabric is completed without an additional adhesive. In an embodiment, a track is integrated into a fabric. In a further embodiment, a track is integrated into a fabric with an adhesive.

In an embodiment, a silicone and/or fluorosilicone rubber in a liquid state when printed in and/or on a fabric is capable of penetrating the orifices of a fabric and anchoring the structure of the track in and/or on the fabric. In an embodiment, a first layer of silicone rubber and/or fluorsilicone rubber is loaded with an electrically conductive material. In a further embodiment, a flexible and/or elastic semi-conductive or conductive material, including, without limitation, silicone rubber and/or fluorsilicone rubber is in a liquid low-viscosity state, a liquid medium-viscosity and/or a liquid high-viscosity state prior to the process of curing. In an embodiment, flexible and/or elastic semi-conductive or conductive material, including, without limitation, silicone rubber and/or fluorsilicone rubber is printed in a fabric when the flexible semi-conductive or conductive material, including, without limitation, silicone rubber is in a liquid low-viscosity state, a liquid medium-viscosity and/or a liquid high-viscosity state and further, without limitation, a flexible semi-conductive or conductive material, including, without limitation, silicone rubber and/or fluorsilicone rubber is bonded to a fabric without an adhesive and penetrates the orifices of the fabric. In an embodiment, a track is integrated into and/or onto a fabric.

Accordingly, in an embodiment, a fabric which comprises at least an elastic and electrically conductive track integrated into the fabric, wherein the elastic and electrically conductive track comprises a flexible semi-conductive or conductive material, including, without limitation, silicone rubber loaded with an electrically conductive material is manufactured according to the following procedure: a) screen-printing, applying a pressure comprising from 0.2 to 0.8 Kg/m², a first coating of silicone rubber loaded with a electrically conductive material on the fabric; b) pre-curing the first coating for up one minute at a temperature of between 80° C. to 200° C.; c) curing the first coating at room temperature; wherein, the thickness of the printed electrically conductive material is from about 120 to 800 µm thick. In an embodiment, the thickness of the elastic and electrically conductive track layer is from about 50 to 800 µm thick, from about 100 to 500 µm thick, from about 120 to 400 µm thick, from about 150 to 300 µm thick, or from about 120 to 180 µm thick. In an embodiment, other alternatives known in the art such as conductive inks can be used as the material for a track.

In an embodiment, the thickness of the printed electrically conductive material is at least 20 µm, at least 30 µm, at least 40 µm, at least 50 µm, at least 60 µm, at least 70 µm, at least 80 µm, at least 90 µm, at least 100 µm, at least 125 µm, at least 150 µm, at least 175 µm, at least 200 µm, at least 225 µm, at least 250 µm, at least 275 µm, at least 300 µm, at least 325 µm, at least 350 µm, at least 375 µm, at least 400 µm, at least 425 µm, at least 450 µm, at least 475 µm, at least 500 µm, at least 525 µm, at least 550 µm, at least 575 µm, at least 600 µm, at least 625 µm, at least 650 µm, at least 675 µm, at least 700 µm, at least 725 µm, at least 750 µm, at least 775 µm, at least 800 µm, at least 825 µm, at least 850 µm, at least 875 µm, at least 900 µm, at least 925 µm, at least 950 µm, at least 975 µm, at least 1000 µm, or more thick. In an embodiment, the thickness of the printed electrically conductive material is no more than 10 µm, no more than 20 µm, no more than 30 µm, no more than 40 µm, no more than 50 µm, no more than 60 µm, no more than 70 µm, no more than 80 µm, no more than 90 µm, no more than 100 µm, no more than 125 µm, no more than 150 µm, no more than 175 µm, no more than 200 µm, no more than 225 µm, no more than 250 µm, no more than 275 µm, no more than 300 µm, no more than 325 µm, no more than 350 µm, no more than 375 µm, no more than 400 µm, no more than 425 µm, no more than 450 µm, no more than 475 µm, no more than 500 µm, no more than 525 µm, no more than 550 µm, no more than 575 µm, no more than 600 µm, no more than 625 µm, no more than 650 µm, no more than 675 µm, no more than 700 µm, no more than 725 µm, no more than 750 µm, no more than 775 µm, no more than 800 µm, no more than 825 µm, no more than 850 µm, no more than 875 µm, no more than 900 µm, no more than 925 µm, no more than 950 µm, no more than 975 µm, no more than 1000 µm, or less thick.

In another embodiment, an electrical conductive area, including, without limitation, a track, is not printed directly into a fabric. In this embodiment, there is a second layer of a flexible and/or elastic material, including, without limitation, a silicone layer and/or a fluorosilicone between a fabric and a conductive area and a second layer of a flexible and/or elastic material, including, without limitation, a silicone and/or a fluorosilicone that is printed into a fabric and is integrated into the fabric as, without limitation, it is able to penetrate the orifices of the fabric and anchor the electronically conductive area in the fibers of the fabric. In an embodiment, a flexible material, including, without limitation, a silicone and/or a fluorosilicone that is loaded with an electrically conductive material is printed over the second flexible and/or elastic material, including, without limitation, a silicone and integrated into a molecular structure of the second flexible material, including, without limitation, a silicone and/or a fluorosilicone by means of chemical bonds. In either case the fabric cohesive strength is improved and a situation where a flexible and/or elastic material, including, without limitation, a silicone and/or a fluorosilicone that is loaded with an electrically conductive material and the second flexible and/or elastic material, including, without limitation, a silicone and/or a fluorosilicone are jointly integrated into the fabric.

In an embodiment an electrically conductive material which is added to a flexible and/or elastic material, including, without limitation, a silicone and/or a fluorosilicone for imparting electric conductivity is selected from carbon fibers, carbon black, nickel coated graphite, copper fibers and mixtures thereof or various metal powders such as silver, nickel, and copper. In an embodiment, the electrically conductive material is a carbon black, such as VP97065/30 (Alpina Technische Produkte GmbH).

In an embodiment the percentage of a conductive material is between 10% to 35%. In another embodiment the percentage of the conductive material is between 15% to 30%. In a further embodiment the percentage of the conductive material is between 20% to 25%. In an embodiment, the percentage of a conductive material is at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95% or at least 100%. In another embodiment, the spandex comprises at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more. In another embodiment, the percentage of a conductive material is no more than 1%, no more than 5%, no more than 10%, no more than 15%, no more than 20%, no more than 25%, no more than 30%, no more than 35%, no more than 40%, no more than 45%, no more than 50%, no more than 55%, no more than 60%, no more than 65%, no more than 70%, no more than 75%, no more than 80%, no more than 85%, no more than 86%, no more than 87%, no more than 88%, no more than 89%, no more than 90%, no more than 91%, no more than 92%, no more than 93%, no more than 94%, no more than 95% or no more than 100%. In another embodiment, the spandex comprises no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15%, no more than 16%, no more than 17%, no more than 18%, no more than 19%, no more than 20%, no more than 25%, no more than 30%, no more than 35%, no more than 40%, no more than 45%, no more than 50%, no more than 55%, no more than 60%, no more than 65%, no more than 70%, no more than 75%, no more than 80%, no more than 85%, no more than 90%, no more than 95% or less.

In another embodiment, as depicted in FIGS. 15A and 15B, the fabric further comprises a coating of an insulating material covering a sensor, including, without limitiation, silicone rubber and/or fluorsilicone rubber that, without limitation, may, but is not required to be loaded with an electrically conductive material. In another embodiment, an insulating material covers a track and/or an electrode. In an embodiment, an insulating material is an anti-slip material, including, without limitation, silicone rubber and/or fluorosilicone rubber. In an embodiment, a fabric of the invention acquires a physiological signal when electrode 3 is placed in contact with the skin of an individual. In another embodiment, a fabric comprises electrode 3 that is placed in contact with the skin of an individual and further wherein, without limitation, an electrical contact is located in track 4.

In an embodiment, when a flexible, elastic and conductive electrode is elongate, a fabric support extends substantially the full length of that layer. In a further embodiment, the flexibility and elasticity of the flexible material, including, without limitation, silicone rubber and/or fluorosilicone rubber, enables the electrode to be held in very good conformity and electrical surface-contact with the patient's skin throughout substantially the whole area during all phases of the flexing and stretching of the sensor in contact with an individual's skin.

In an electrocardiogram (ECG) measurement, the contact resistance between the skin of an individual, including, without limitation, a human body and the electrodes can be about several MO. In an embodiment, a resistance value, from an electrode through a track to an electrical connector or back is 1000 KΩ or less, wherein a track comprises a flexible and/or elastic material, including, without limitation, a silicone rubber and/or fluorosilicone rubber loaded with an electrically conductive material. In an embodiment, a sensor is sufficient for practical use when the flexible and/or elastic material used in a track, including, without limitation, silicone rubber and/or fluorosilicone rubber loaded with electrically conductive material that is stretched by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 4647%, 48%, 49%, 50% or more.

In a further embodiment, a resistance value, from one end of a sensor, (electrical connector to an electrode or an electrode to an electrical connector), wherein a track is comprising a flexible and/or elastic material, including, without limitation, a silicone rubber and/or fluorosilicone rubber loaded with electrically conductive material, is less than 50 KΩ, 100 KΩ, 150 KΩ, 200 KΩ, 250 KΩ, 300 KΩ, 350 KΩ, 400 KΩ, 450 KΩ, 500 KΩ, 550 KΩ, 600 KΩ, 650 KΩ, 700 KΩ, 750 KΩ, 800 KΩ, 850 KΩ, 900 KΩ, 950 KΩ or 1000 KΩ when the flexible and/or elastic material, including, without limitation, silicone rubber loaded with electrically conductive material is stretched by about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more.

In a embodiment, the electrical resistance per cm of a flexible and/or elastic material, including, without limitation, silicone rubber and/or fluorosilicone rubber loaded with an electrically conductive material is 1000 KΩ/cm or less, or in a further embodiment, 500 KΩ/cm or less. In another embodiment, the electrical resistance per cm of a flexible and/or elastic material, including, without limitation, silicone rubber and/or fluorosilicone rubber loaded with an electrically conductive material is comprising from 50 Ω/cm to 100 kΩ/cm, and in a further embodiment, 1 KΩ/cm to 100 KΩ/cm, and in another embodiment, the resistance per cm value is comprising from 50 Ω/cm to 10 KΩ/cm. In a further embodiment, the electrical resistance per cm of a flexible and/or elastic material, including, without limitation, silicone rubber and/or fluorosilicone rubber loaded with an electrically conductive material that is less than 1 KΩ/cm, less than 2 KΩ/cm, less than 3 KΩ/cm, less than 4 KΩ/cm, less than 5 KΩ/cm, less than 6 KΩ/cm, less than 7 KΩ/cm, less than 8 KΩ/cm, less than 9 KΩ/cm, less than 10 KΩ/cm, less than 11 KΩ/cm, less than 12 KΩ/cm, less than 13 KΩ/cm, less than 14 KΩ/cm, less than 15 KΩ/cm, less than 16 KΩ/cm, less than 17 KΩ/cm, less than 18 KΩ/cm, less than 19 KΩ/cm, less than 20 KΩ/cm, less than 21 KΩ/cm, less than 22 KΩ/cm, less than 23 KΩ/cm, less than 24 KΩ/cm, less than 25 KΩ/cm, less than 26 KΩ/cm, less than 27 KΩ/cm, less than 28 KΩ/cm, less than 29 KΩ/cm, less than 30 KΩ/cm, less than 31 KΩ/cm, less than 32 KΩ/cm, less than 33 KΩ/cm, less than 34 KΩ/cm, less than 35 KΩ/cm, less than 36 KΩ/cm, less than 37 KΩ/cm, less than 38 KΩ/cm, less than 39 KΩ/cm, less than 40 KΩ/cm, less than 41 KΩ/cm, less than 42 KΩ/cm, less than 43 KΩ/cm, less than 44 KΩ/cm, less than 45 KΩ/cm, less than 46 KΩ/cm, less than 47 KΩ/cm, less than 48 KΩ/cm, less than 49 KΩ/cm, less than 50 KΩ/cm, 55 KΩ/cm, less than 60 KΩ/cm, less than 65 KΩ/cm, less than 70 KΩ/cm, less than 75 KΩ/cm, less than 80 KΩ/cm, less than 85 KΩ/cm, less than 90 KΩ/cm, less than 95 KΩ/cm, less than 100 KΩ/cm, 150 KΩ/cm, 200 KΩ/cm, 250 KΩ/cm, 300 KΩ/cm, 350 KΩ/cm, 400 KΩ/cm, 450 KΩ/cm, 500 KΩ/cm, 550 KΩ/cm, 600 KΩ/cm, 650 KΩ/cm, 700 KΩ/cm, 750 KΩ/cm, 800 KΩ/cm, 850 KΩ/cm, 900 KΩ/cm, 950 KΩ/cm or 100 KΩ/cm.

In another embodiment, the cured temperature of a silicone rubber and/or fluorosilicone rubber loaded with an electrically conductive material is between 20° C. to 200° C. In a further embodiment, the cured temperature is between 50° C. to 140° C. In another embodiment the cured temperature is between 100° C. to 120° C. In an embodiment, the cured temperature of a silicone rubber loaded with an electrically conductive material is no more than 5° C., no more than 10° C., no more than 15° C., no more than 20° C., no more than 25° C., no more than 30° C., no more than 35° C., no more than 40° C., no more than 45° C., no more than 50° C., no more than 55° C., no more than 60° C., no more than 65° C., no more than 70° C., no more than 75° C., no more than 80° C., no more than 85° C., no more than 90° C., no more than 95° C., no more than 100° C., no more than 110° C., no more than 120° C., no more than 130° C., no more than 140° C., no more than 150° C., no more than 160° C., no more than 165, no more than 170° C., no more than 180° C., no more than 190° C., no more than 200° C., no more than 210° C., no more than 220° C., no more than 230° C., no more than 240° C., no more than 250° C., no more than 260° C., no more than 270° C., no more than 280° C., no more than 290° C. or no more than 300° C.

In an embodiment, a silicone rubber and/or fluorosilicone rubber loaded with an electrically conductive material contains a platinum catalyst, diorganopolysiloxane having silicon-bonded alkenyl groups, organohydrogenpolysiloxane and an electrically conductive material.

In an embodiment, a silicone rubber loaded with an amount between 5% w/w to 40% w/w of an electrically conductive material comprises: a) diorganopolysiloxane having silicon-bonded alkenyl groups; b) organohydrogenpolysiloxanes; c) a platinum catalyst; and d) an electrically conductive material.

In a further embodiment, examples of the diorganopolysiloxane having silicon-bonded alkenyl groups are, without limitation, dimethylvinylsiloxy-terminated dimethylpolysiloxane gums, dimethylallylsiloxy-terminated dimethylpolysiloxane gums, phenylmethylvinylsiloxy-terminated diphenylsiloxane-dimethylsiloxane copolymer gums, dimethylvinylsiloxy-terminated methylvinyloxane-dimethylsiloxane copolymer gums and silanol-terminated methylvinylsiloxane-dimethylsiloxane copolymer gums.

In another embodiment, examples of the organohydrogenpolysiloxanes are, without limitation, trimethylsiloxy-terminated methylhydrogenpolysiloxanes, trimethylsiloxy-terminated dimethylsiloxane-methylhydrogensiloxane copolymers, dimethylphenylsioxy-terminated methylphenylsiloxanemethyl-hydrogensiloxane copolymers, cyclic methylhydrogenpolysiloxanes and copolymers composed of dimethylhydrogensiloxy units and $SiO_{4/2}$ units.

In an embodiment, and without limitation, a platinum catalyst known as a curing acceleration catalyst for a silicone composition which cures by a hydrosilation reaction, include, without limitation, platinum black, platinum on active carbon, platinum on silica micropowder, chloroplatinic acid, alcohol solutions of chloroplatinic acid, platinum olefin complexes, platinum tetrachloride, platinum vinylsiloxane complexes, chloroplatinic acid-olefin complexes, chloroplatinic acid methylvinylsiloxane complexes.

In an embodiment, a silicone rubber loaded with an amount between 5% w/w to 40% w/w of a electrically conductive material comprises: a) divinylpolydimethylsiloxane in a percentage between 60% w/w to 75% w/w; b) dioxosilane in a percentage between 7% w/w to 15% w/w, c) carbon black in a percentage between 5% w/w to 15% w/w, d) platinum (0)-1,3-divinyl-1,1,3,3-tetramethyl disiloxane (CAS No. 68478-92-2) in a percentage between 0.001% w/w to 0.05% w/w and; e) polydimethylthydrogensiloxane in a percentage between 3% w/w to 7% w/w.

In an embodiment, a preparation process of the fabric of the invention comprises the steps of a) liquid-printing a first coating of a silicone rubber loaded with an amount between 5% w/w to 40% w/w of a electrically conductive material on the fabric; b) pre-curing the first coating for up one minute at a temperature of at between 80° C. to 200° C.; and c) curing the first coating at room temperature.

In an embodiment, a garment comprises a circuit, including, without limitation, a circuit board, with elastic and flexibility mechanical properties, where the circuit board is a fabric mesh and a wiring system is conductive silicone printed on the fabric of the garment. In an embodiment, an electronic component to be placed in a flexible semi-conductive or conductive material, including, without limitation, a silicone rubber and/or fluorosilicone rubber, must be placed in the flexible material, including, without limitation, silicone rubber and/or fluorosilicone rubber, prior to its curing. In an embodiment, in order to use the flexible material, including, without limitation, silicone rubber and/or fluorosilicone rubber as a wiring system the electronic components may be place in the fabric before applying the liquid semi-conductive or conductive flexible material, including, without limitation, a silicone rubber and/or fluorosilicone rubber. This method is described in an embodiment comprising the following steps: a) coating the electrode with a thermal adhesive; b) fixing the electrode to the fabric; c) liquid-printing a first layer of silicone rubber loaded with an amount between 5% w/w to 40% w/w of a electrically conductive material on the fabric; d) pre-curing the first layer for up one minute at a temperature of at between 80° C. to 200° C.; e) coating a layer of an insulating material covering the first layer of the silicone rubber loaded with an electrically conductive material; f) curing at room temperature; g) putting the connector.

In another embodiment, a first layer of a flexible material, including, without limitation, a silicone rubber and/or fluorosilicone rubber, is loaded with an electrically conductive material that is screen-printed with a thickness comprising from 120-800 µm, of from 200-500 µm or of from 300-400 µm.

In another embodiment an electrically conductive material is screen-printed with a thickness of at least 25 µm, 50 µm, 75 µm, 100 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, 300 µm, 325 µm, 350 µm, 375 µm, 400 µm, 425 µm, 450 µm, 475 µm, 500 µm, 525 µm, 550 µm, 575 µm, 600 µm, 625 µm, 650 µm, 675 µm, 700 µm, 725 µm, 750 µm, 775 µm, 800 µm, 825 µm, 850 µm, 875 µm, 900 µm, 925 µm, 950 µm, 975 µm, 1000 µm, or more. In another embodiment an electrically conductive material is screen-printed with a thickness of no more than 25 µm, 50 µm, 75 µm, 100 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, 300 µm, 325 µm, 350 µm, 375 µm, 400 µm, 425 µm, 450 µm, 475 µm, 500 µm, 525 µm, 550 µm, 575 µm, 600 µm, 625 µm, 650 µm, 675 µm, 700 µm, 725 µm, 750 µm, 775 µm, 800 µm, 825 µm, 850 µm, 875 µm, 900 µm, 925 µm, 950 µm, 975 µm, 1000 µm, or less.

In an embodiment, the method of preparation of the track and electrical connector assembly comprises: a) die cut at least one conductive support base; b) fix the at least one conductive support base to a fabric support with a textile adhesive, including, without limitation, a holt melt adhesive applying pressure and heating from 80°-185° C., including, without limitation, 110-165° C., for 5-30 seconds, including, without limitation, 10-20 seconds; screen-printing a conductive silicone rubber on the textile fabric substrate, while partially treading in the at least one shaped end, including, without limitation, a shaped end, including, without limitation, a round shaped end of the conductive support base, applying a pressure comprising from 0.2 to 0.8 Kg/m². In an embodiment, the steps a) and b) describe a process for the preparation of an electrode, the steps c) to f) describe a process for the preparation of an electrically conductive area (track). In an embodiment, the process for the preparation of an electrically conductive area (track), steps c) to g) can be carried out before the process of preparing an electrode steps a) and b).

Figure 20:
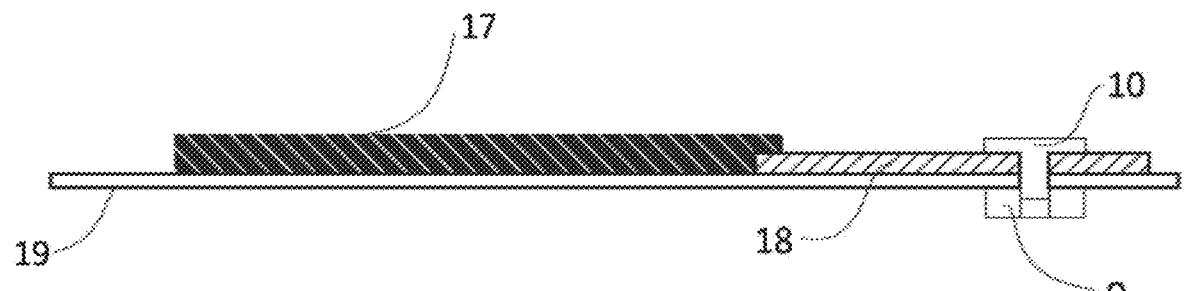
FIG. 20 illustrates cross-section of track (17) and support base (18) assembly arranged on a textile fabric substrate (19), wherein the support base is in electrical contact with a rigid electrical component comprising two parts (9 and 10).
Figure 21:
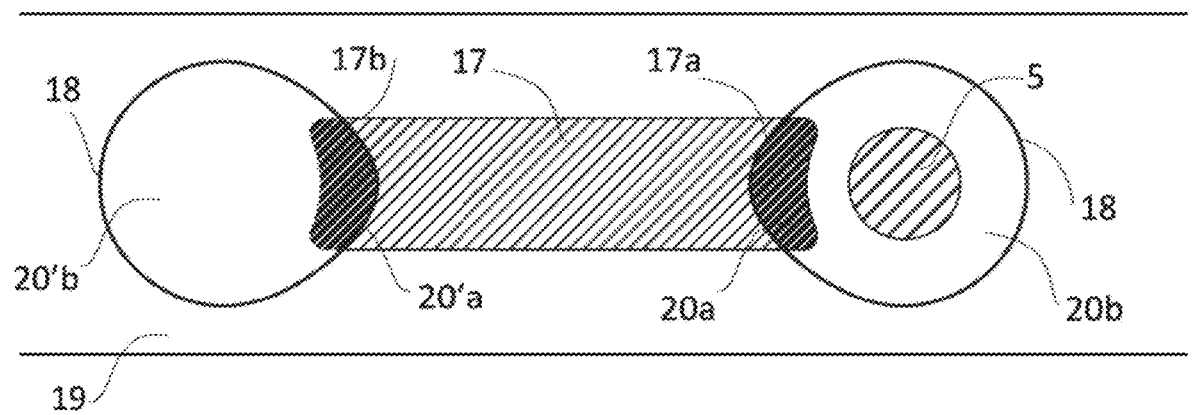
FIG. 21 illustrates elevation view of the assembly disclosed herein wherein both ends of the track (17a and 17b) are treading on two different support bases (20a and 20'a), and a rigid electrical component (5) is arranged on the non-treaded area (20b) of one of the support bases.
Figure 24:
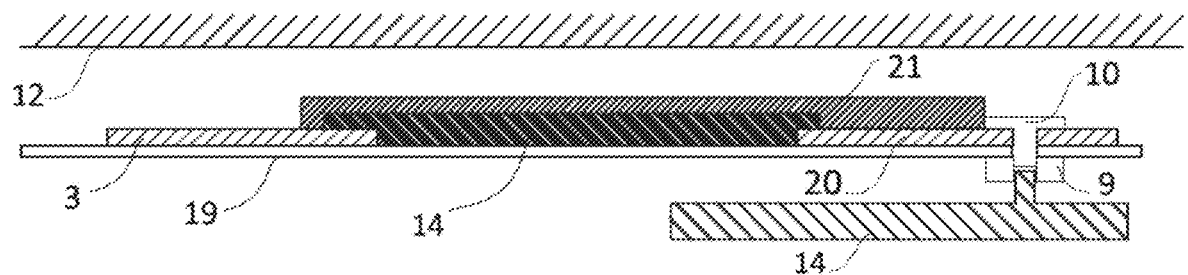
FIG. 24 illustrates cross-section view of a sensor according to an embodiment.

FIG. 21 depicts a flexible conductive support base comprises two areas, one being treaded by elastic semi-conductive or conductive track 20a and the other one 20b either being adapted to connect a rigid electrical component or being adapted to be used as an electrode. FIGS. 20, 21 and 24 depict an elastic semi-conductive track and flexible conductive support base assembly wherein, each end of track 20a and 20'a are treading on two different flexible conductive support bases 20 and 20'. In another embodiment, non-treaded area 20'b of one of flexible conductive support bases 18, is adapted to be used as electrode 20'b and on non-treaded area 20b of the other flexible conductive support base there is arranged rigid electrical component 5. In another embodiment, an elastic semi-conductive track and flexible conductive support base assembly comprises one end of track 17a that is treading on the at least one shaped end, including, without limitation, round shaped end 20a of one flexible conductive support base 18, whereas on non-treaded area 20b of such support base there is arranged rigid electrical component 5; and the other end of track 17b is adapted to be in electrical contact with an electrode.

In another embodiment, a rigid electrical component 5 can be arranged in electrical contact with a sensor. In a further embodiment, and without limitation, an electrical component includes, without limitation, electrical connectors, switches, resistors, capacitors, passive components (protection devices), magnetic (inductive) devices, piezoelectric devices, crystals, resonators, power sources, semiconductors (diodes, transistors, integrated circuits, optoelectronic devices), display devices, antennas, transducers, sensors, electrochemical sensors, detectors and electrodes.

Figure 22:
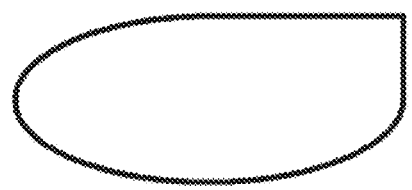
FIG. 22 illustrates teardrop-like shape of the support base according to an embodiment.

As depicted in FIGS. 20, 21, 22 and 24, a conductive support base 18 is a flexible and conductive textile comprising conductive and non-conductive fibres, having at least one of its ends 20a, the end which is treaded by the track, round shaped, being in an embodiment, and without limitation, a teardrop-like shape as depicted in FIG. 22. In another embodiment, the shape and dimension of a track may vary and it is not limited by the manufacturing process of the fabric substrate.

In an embodiment, a conductive support base has a teardrop-like shape, wherein a connection edging between the support base and a track has a shaped end, including, without limitation, a round shaped end that can, without limitation, improve the mechanical resistance to stretching, minimizing or substantially avoiding tearing the joints when the track is stretched, twisted, folded and/or squeezed while used. Furthermore, the circuit design is simplified since the support base can be guided to the track direction and vice versa.

According to an embodiment, the conductive support base is attached to a fabric with a (textile) fabric adhesive. In another embodiment, a (textile) fabric adhesive includes, without limitation, any suitable hot-melt adhesive for use in a (textile) fabric. In an embodiment, a track is elastic and flexible. In another embodiment, the elasticity and flexibility of an electrically conductive track provides, without limitation, that conductivity is not interrupted with the movement of the fabric. A track may be provided to a fabric in any manner known in the art, including, without limitation, to a surface of the fabric substrate through screen-printing methods.

As depicted in FIG. 21, placing rigid electrical component 5, for instance, without limitation, an electrical connector, on the conductive support base 18, which is electrically in contact with the elastic and semi-conductive track 17 instead of directly in contact with the track, results in an improvement of, without limitation, the mechanical properties of the assembly, avoiding the textile being torn when stretching.

In an embodiment, a conductive support base is used as a conductive foot print which is in electrical contact with the elastic and electrically conductive track that functions, without limitation, as a conductive support base wherein rigid electrical component 5 is arranged. In an embodiment, if a flexible conductive support base is elastic, the assembly will work perfectly on its own, but when a rigid electrical component is in placed, such as, without limitation, an electrical connector, the stress will move from the joint between track and support base to the joint between the support base and rigid electrical component. This results in the mechanical properties of a joint between an elastic and a rigid element being low as the assembly suffers mechanical stress. When the assembly is integrated into a textile, the mechanical properties of the joints between the different materials are crucial to obtain a proper electrical circuit.

In an embodiment, a track is integrated into a fabric and partially into an at least one round shaped end of a conductive support base by anchoring the flexible material, including, without limitation, silicone with the structure of the fibers of the textile. In an embodiment, a silicone rubber and/or a fluorosilicone rubber is cured into a fabric. In a further embodiment, a silicone rubber and/or a fluorosilicone rubber is cured into a garment.

In an embodiment, when it is required to decrease the time of a curing process, a step of pre-curing by heating the silicone rubber at a temperature comprising from 80° C. to 200° C. is included. In another embodiment, a pre-curing step is carried out at a temperature comprising from 90° C. to 165° C.

As depicted in FIGS. 20, 21 and 24, a flexible material, including, without limitation, a silicone rubber loaded with a conductive material is screen-printed on a fabric 19, while treading partially on the one round shaped end 20a of the conductive support base 18; resulting in the flexible material, including, without limitation, the silicone rubber penetrating into the orifices of the fabric, and the flexible material, including, without limitation, silicone rubber being anchored with the structure of the fibers of the textiles when cured at room temperature after being screen-printed on the fabric. In another embodiment, the flexible semi-conductive track 17 is provided to the surface of the fabric 19 and the at least one round shaped end 20a of the conductive support base 18 includes a screen-printed flexible material, including, without limitation, a silicone rubber and/or fluorosilicone rubber loaded with an electrically conductive material, and further wherein, a step of applying pressure when applying the flexible material, including, without limitation, the silicone rubber directly to the fabric and the at least one shaped end, including, without limitation, a round shaped end of the conductive support base, in order to eliminate any air bubble that will break and/or impede the conductivity. In an embodiment, a screen-printing process uses low speed and high pressure. In an embodiment, a pressure to be applied comprises from 0.2 to 0.8 Kg/m$^2$, from 0.3 to 0.5 Kg/m$^2$; or about 0.45 Kg/m$^2$. In another embodiment, a pressure to be applied comprises at least 0.1 Kg/m$^2$, at least 0.2 Kg/m$^2$, at least 0.3 Kg/m$^2$, at least 0.4 Kg/m$^2$, at least 0.5 Kg/m$^2$, at least 0.6 Kg/m$^2$, at least 0.7 Kg/m$^2$, at least 0.8 Kg/m$^2$, at least 0.9 Kg/m$^2$, at least 1 or more Kg/m$^2$. In another embodiment, a pressure to be applied comprises at least 0.1 Kg/m$^2$, at least 0.2 Kg/m$^2$, at least 0.3 Kg/m$^2$, at least 0.4 Kg/m$^2$, at least 0.5 Kg/m$^2$, at least 0.6 Kg/m$^2$, at least 0.7 Kg/m$^2$, at least 0.8 Kg/m$^2$, at least 0.9 Kg/m$^2$, at least 1 or more Kg/m$^2$.

A textile comprises, without limitation, any kind of woven, knitted, or tufted cloth, or a non-woven fabric (e.g. a cloth made of fibers that have been bonded into a fabric). A textile further comprises, without limitation, yarns, threads and wools that can be spun, woven, tufted, tied and otherwise used to manufacture cloth. An, "elastic material" is, without limitation, a material which relatively easily may be stretched or compressed and is able to resume its original shape after being stretched or compressed or resume close to its original shape after being stretched or compressed.

In an embodiment, an electrical connector includes, without limitation, electrically conductive fasteners. In a further embodiment, and electrically conductive fastener is, without limitation, a press stud (also sometimes referred to as a snap, a snap fastener, or a popper). In a further embodiment, a press stud is, without limitation, made of a pair of interlocking discs. As depicted in FIG. 24, a circular lip under one disc 10 fits into a groove on the top of the other 9, holding them fast until an amount of force is applied. In an embodiment, a press-stud is, without limitation, attached to fabric by hammering, plying, or sewing. In a further embodiment, other kinds of fasteners may be used, including, without limitation, a magnet, a pin-socket or a plug-socket connection (e.g. with the socket being provided on the sensor apparatus), a conductive Velcro® or other conductive metal clip fasteners. Any kind of a fastener that allows, without limitation, an electronic device to be easily attached and detached may be used. In an embodiment, in use said electronic device is attached, without limitation on the outside of the garment and may be easily attached and detached by a user.

As depicted in FIGS. 21 and 24, a sensor is adapted to be incorporated in a garment, the sensor comprising an assembly comprising, an electrode, either the non-treaded area 20'b of one of the two flexible conductive support bases 18 when each end of the track 17a and 17b are treaded in two different support bases 18 or an electrode in electrical contact with the second end of the track 17b when only one support base is present; the electrode being adapted to obtain physiological signals through its contact with skin 12 of the wearer of the garment, for example, without limitation a human.

As further depicted in FIGS. 20, 21 and 24, a sensor is that wherein track 17 is electrically isolated from its contact with skin 12 of the wearer of the garment, and rigid electrical component 5 is an electrical connector adapted to transmit a physiological signal obtained through electrode 3 to electronic instrument 14. The track is covered with insulating material 8, including, without limitation, an isolating silicone rubber. Flexible conductive support base 18 is attached to fabric 19 with an adhesive, including, without limitation, a holt-melt adhesive.

Figure 23:
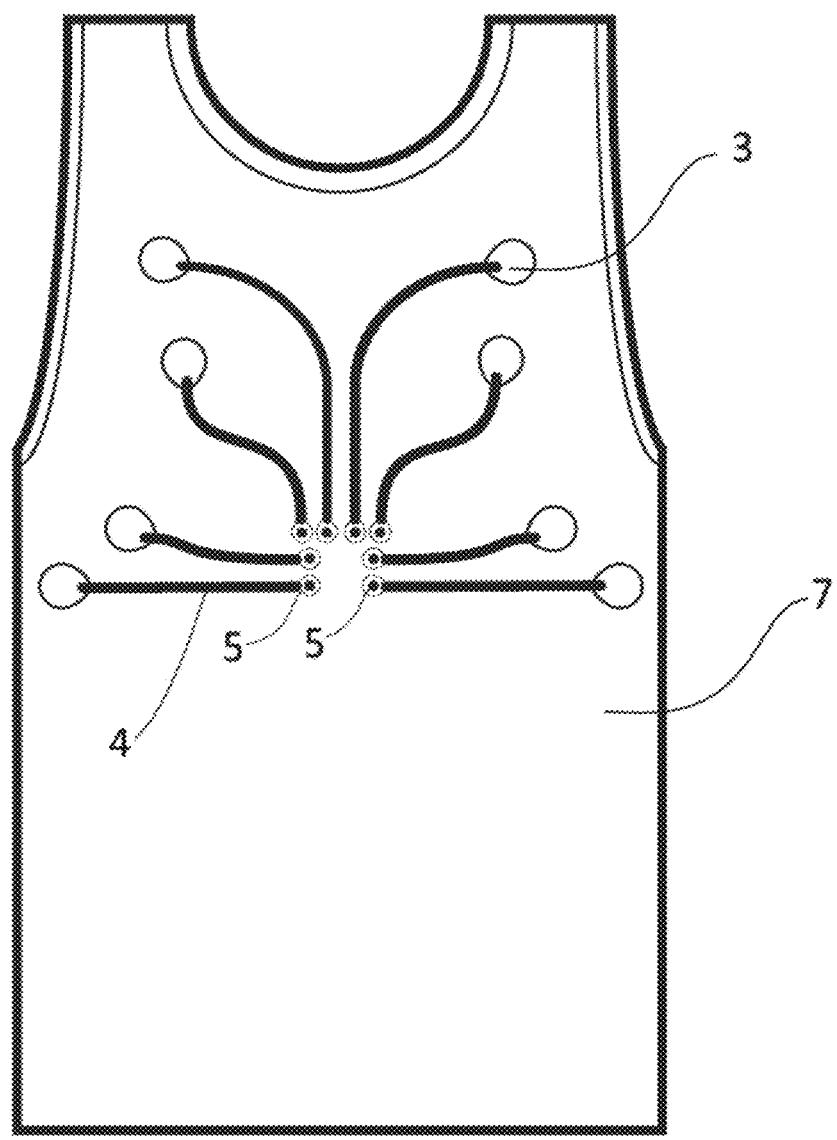
FIG. 23 illustrates elevation view of the garment according to an embodiment.

Depicted in FIG. 23 is garment 7 comprising multiple sensors 1, each with electrode 3, track 4, and electrical connectors, including those depicted as 5 and 5'. In an embodiment, garment 7 can include, without limitation, one or more sensors 1 wherein tracks 4 of the sensors are printed on garment 7 in any manner, including, without limitation, a straight line, a curved line or other shape.

In an embodiment, a device comprising at least one sensor and an electronic instrument for receiving, collecting, storing, processing and/or transmitting data from said sensor is herein provided. In another embodiment, a garment comprising a device is herein provided. In a further embodiment, the device is arranged in the garment such that in use the device is arranged substantially in an area which comprises a suitable location for measuring of various parameters, including, an individual's electrocardiogram (ECG).

EXAMPLES

Example 1

In this experiment the following garments were used: ZEPHYR™ HxM (made by Zephyr Technology Corporation) (I), Polar TEAM² (made by Polar Electro, OY.) (II), NUMETREX® Cardio-Shirt (made by Textronics, Inc.) (Ill) and a shirt of the invention (IV), wherein the shirt of the invention included a track and the electrode that were made of conductive fabric and the electrode area has the orifices filled with silicone rubber. The NUMETREX® Cardio-Shirt is a shirt with textile electrodes knitted into the fabric. The ZEPHYR™ HxM strap and Polar TEAM² strap are straps with textile electrodes. The ZEPHYR™ HxM strap includes an electrode and a resilient compressible filler provided between the garment and the electrode such that, in use, the electrode is held substantially in place against the skin when the garment moves relative to the user's skin. The Polar TEAM² strap includes a contact layer including conductive fibres, and a moisture layer for retaining moisture on top of the contact layer.

The test protocol was divided into different levels of physical exigency: resting, daily activity and strong physical activity. Each test subject was monitored with a device compatible with all the straps and shirts tested. The exercises of the protocol were defined as following:

(I) Resting (A): the subject remained in a lying down position on a table for 30 seconds.
(II) Daily activity included each of the following activities: (1) Standing (B): the subject stood on their feet for 20 seconds without moving; (2) Sitting down/standing up (C): the subject sat down and stood up from a chair 4 times, remaining 3 seconds in each state; (3) Bending down (D): the subject bent down 3 times, always in the same way (without flexing their knees); (4) Arm movement (E): the subject moved their arms in different directions (straight, horizontal and vertical) 3 times each; and (5) Walking (F): The subject walked at a approximate speed of 3 km/h for 20 seconds.
(III) Strong Physical Activity (H) is defined by: (1) Moderate-speed Running (I): the subject ran at a speed of 6 km/h during 20 seconds; (2) Fast-speed Running (J): the subject sped up his pace until he reached 10 km/h, then he stayed running at this speed during 15 seconds; (3) Strong arm movement (racket move) (K): the subject moved his arm strongly simulating hitting a ball with a racket (with both arms), doing this movement 5 times; (4) Torso turning (L): keeping the feet in the same position, the subject turned his torso in both directions, 5 times each; (5) Jumping (M): the subject jumped high, he will run two or three meters and then he will jumped again. He repeated this movement 5 times.

Strong physical activity was more physically demanding than the daily activity. All the exercises done in the resting and daily activities were with the strap or shirt put directly onto the subject (no sweat) and all the strong physical activity was done with the strap or shirt worn by the subject where had sweated. When the different electrocardiographic signals were obtained with each shirt or strap were performed a sort of measures over these signals to evaluate the different technologies. The measures performed on the signals were (for each exercise of each activity):

Visual Measures

This measure is a direct recognition, just by watching the signal, of the quality of the signal acquired in terms of morphology and beats detected. This visual recognition is also used to identify what beats (QRS complexes) are recognizable as beats and which of them are too noisy to be recognized by a cardiologist. A total of 250 beats were analyzed for resting and Daily Activity and for Strong Physical Activity a total of 500 beats were analyzed.

Measures Over the Signal

These measures were made on the signal registered in each exercise of each activity session. These measures involve manual and automatic analysis of the recorded signals.

Autocorrelation:

The signal was segmented each 3 seconds with an overlap of 2 seconds between blocks and the autocorrelation was done of each block. This measure follows the formula:

$$R_x(m) = (1/N - |m|)\sum_{n=0}^{N-1} x_n x_{n+m}$$

where x is a signal of N samples. Then it's normalized regarding to the value of $R_x(0)$. Next. the autocorrelation maximum that it's not the one in $R_{x\ norm}$ (0) is obtained. At this point, it is believed that there is a maximum at this point because the signal is compared to itself without shift.

This index give us a measure of how much the signal resembles a shift to itself (starting from the premise that a heartbeat and the next one are very similar). In this way, values close to 1 show that the signal is very similar to a shifted copy of itself, so it's clean of noise, while low values show that the signal is corrupted by noise.

T-P Segment RMS:

The RMS (Root Mean Square) of the T-P segment was calculated in between heartbeats (aprox. 20 segments). This measure was done for each exercise and, averaged, give an estimate of the noise in the signal, particularly in Resting state, because the T-P segment is isoelectric.

These measures were done manually (to select the beginning and end of each segment). In those signals where the T wave was not present (ZEPHYR™ HxM and Polar TEAM² straps and NUMETREX® Cardio-Shirt in Resting and Daily Activity), the segment is defined between two consecutive heartbeats. This value has to be as low as possible but has to be contextualized with the QRS amplitude (see the point RMS/AmplitudeRS).

Maximum T-P Segment:

It measures the maximum peak of noise of the different T-P segments. This value was useful to see if high peaks of noise contaminate our signal.

Maximum Amplitudes:

The amplitudes of the QRS peaks were measured (R peaks and S peaks, to get RS amplitude) for the beats of each exercise. There was not a preferred value but higher values tend to be better to low ones (low ones are more prone to noise).

RMS/AmplitudeRS:

This factor was calculated with the measures explained in the previous points. This index gives an accurate idea of the noise of the system in the different exercises. It is normalized to the RS Amplitude because each shirt/strap captures a different amount of signals, different amplitudes, so RMS in the T-P segment has to be contextualized to each sensor strap or shirt. In general, a lower value is better.

Of all the index and values obtained, the most important ones are RMS/AmplitudeRS and Autocorrelation because both of them are very good indicators of the noise that contaminate the signals and how recognizable are the heartbeats in the registered signals.

The results were divided into and presented as three sections: results for Resting Activity, Daily Activity and Strong Physical Activity.

Resting and Daily Activity

Figure 6:
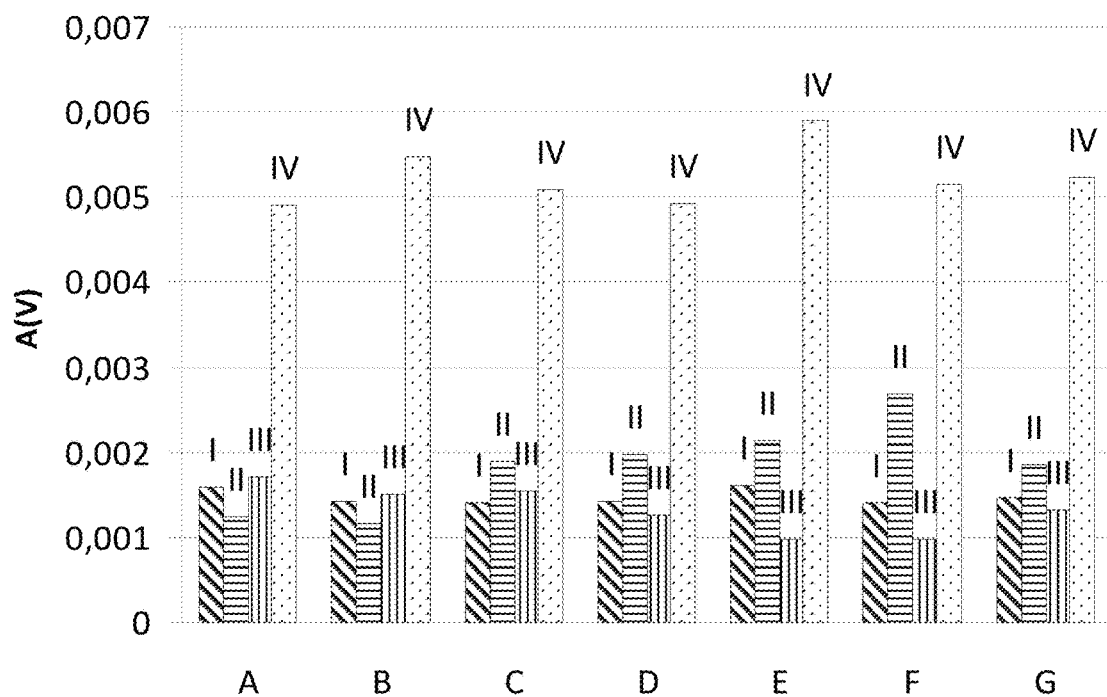
FIG. 6 shows Amplitude RS (A(v)) in resting (A), stand (B), stand/sit (C), bend (D), arms (E), walk (F), and all the activities, resting, stand stand/sit, bend arms and walk (G) for ZEPHYR™ HxM strap (I), Polar TEAM$^2$ strap (II), NUMETREX® Cardio-Shirt (III) and the shirt of the invention (IV).

FIG. 6 depicts the amplitude RS (A(v)) in resting (A), stand (B), stand/sit (C), bend (D), arms (E), walk (F), and all the activities, resting, stand stand/sit, bend arms and walk (G) for ZEPHYR™ HxM strap (I), Polar TEAM² strap (II), NUMETREX® Cardio-Shirt (III) and a shirt of the invention (IV). The amplitude RS gives an idea of the signal captured by the system and it is understood that a high amplitude RS is better than a lower one. As depicted in FIG. 6, the shirt of the invention was able to capture the signal more efficiently and better than the other garments. It also worked better in dry conditions as this activity session does not involve sweating.

Figure 7:
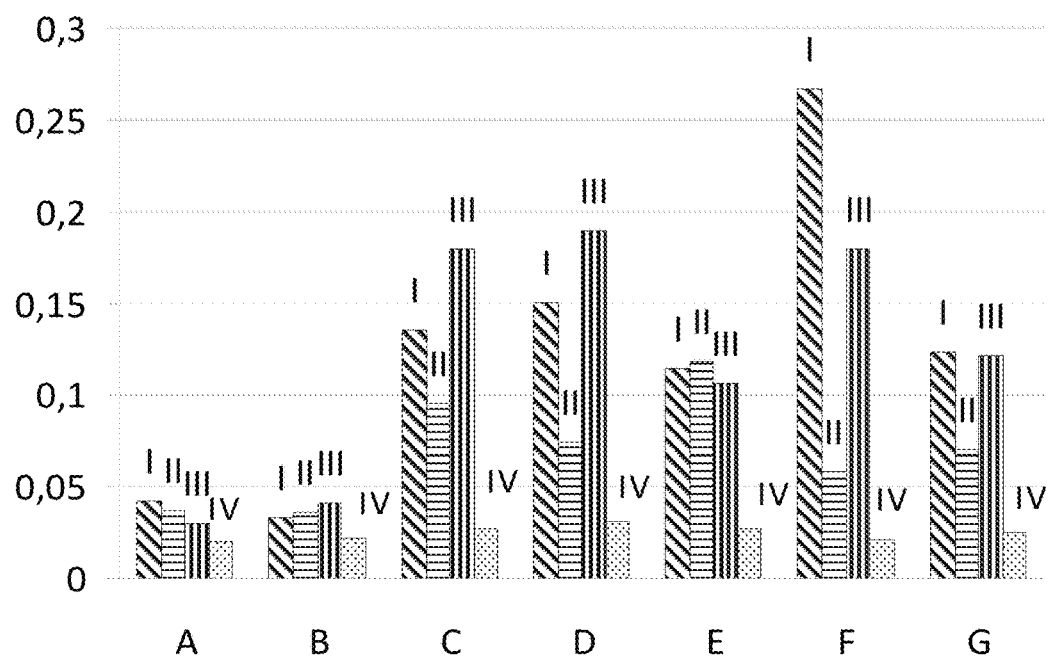
FIG. 7 shows RMS/Amplitude RS in resting (A), stand (B), stand/sit (C), bend (D), arms (E), walk (F), and all the activities, resting, stand stand/sit, bend arms and walk (G) for ZEPHYR™ HxM strap (I), Polar TEAM$^2$ strap (II), NUMETREX® Cardio-Shirt (III) and the shirt of the invention (IV).

FIG. 7 depicts RMS/Amplitude RS in resting (A), standing (B), standing/sitting (C), bending (D), arms (E), walking (F), and resting and daily activity (resting, standing, standing/sitting, bending arms and walking) (G) for ZEPHYR™ HxM strap (I), Polar TEAM² strap (II), NUMETREX® Cardio-Shirt (III) and the shirt of the invention (IV). This data has value as the noise is contextualized regarding the AmplitudeRS, and it's a good measure of the SNR (Signal-to-Noise Ratio) of the system. The value calculated here is Noise-to-Signal, so the lower this value the better. As depicted in FIG. 7, the shirt of the invention (IV) showed the lowest value.

Figure 8:
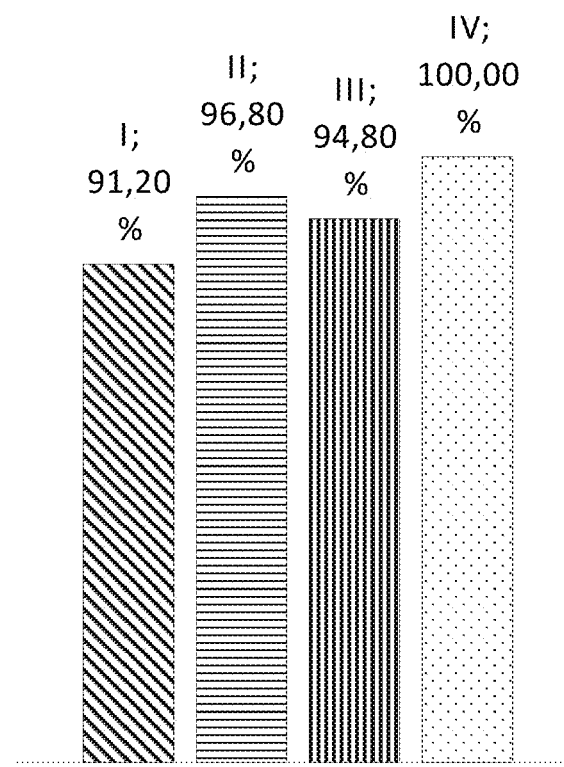
FIG. 8 shows percentage of good QRS complex in resting and daily activity for ZEPHYR™ strap (I), Polar strap (II), NUMETREX® shirt (III) and the shirt of the invention (IV).

FIG. 8 depicts the percentage of a good QRS complex in resting and daily activity for ZEPHYR™ HxM strap (I), Polar TEAM² strap (II), NUMETREX® Cardio-Shirt (III) and the shirt of the invention (IV). FIG. 8 depicts how many beats are recognizable as QRS at first sight. A total of 250 beats were analyzed for each system, and the results depict the total of the Resting and Daily Activity Session (not divided into exercises). The higher the percentage the better. The highest value was found for the shirt of the invention (IV).

Figure 9:
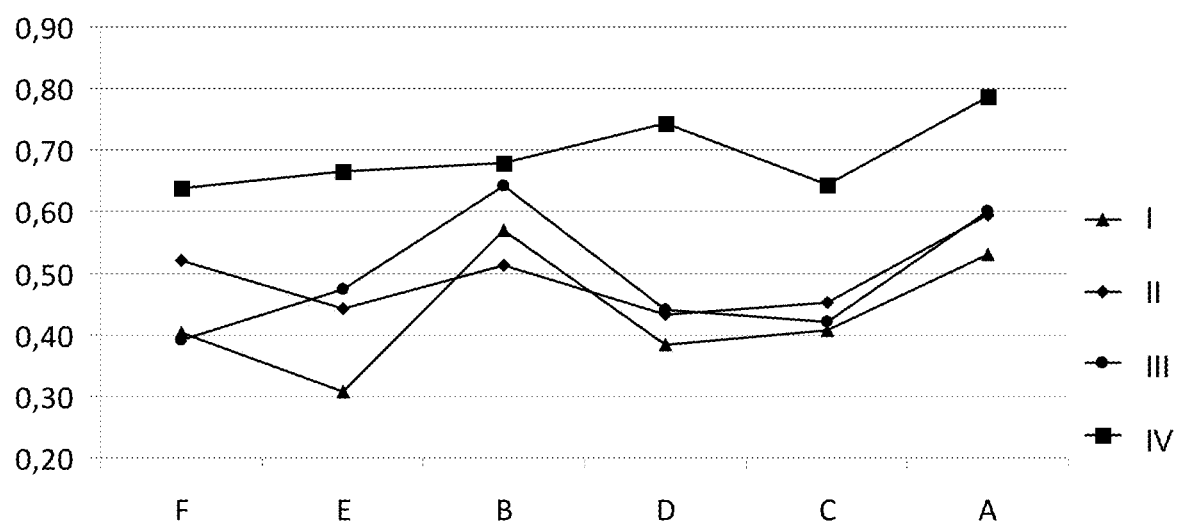
FIG. 9 shows autocorrelation value for ZEPHYR™ HxM strap (I), Polar TEAM$^2$ strap (II), NUMETREX® Cardio-Shirt (III) and the shirt of the invention (IV), in walking (F), arms (E), stand (B), bend (D), stand/sit (C) and resting (A).

FIG. 9 depicts the autocorrelation value for ZEPHYR™ HxM strap (I), Polar TEAM² strap (II), NUMETREX® Cardio-Shirt (III) and the shirt of the invention (IV) in walking (F), arms (E), standing (B), bending (D), standing/sitting (C) and resting (A). This information provides a good indicator of the quality, reproducibility and the similitude between the heartbeats. The closer this value is to 1, the better. The shirt of the invention had the closest value to 1.

Strong Physical Activity

FIG. 10 depicts the Amplitude RS (A(v)) in mid-speed (H), fast-speed (I), torso-moving (J), racket (K), jumping (L), and all the activities, (mid-speed, fast-speed, torso moving, racket and jumping) (M) ZEPHYR™ HxM strap (I), Polar TEAM² strap (II), NUMETREX® Cardio-Shirt (III) and the shirt of the invention (IV). In Strong Physical Activity, likely as a result of the buildup of sweat on the test subject, the amplitude of the signal does not differ greatly between technologies, as the sweat helps the conduction of the electric potentials to the electrode and decreases the impedance of the skin-electrode interface.

Figure 11:
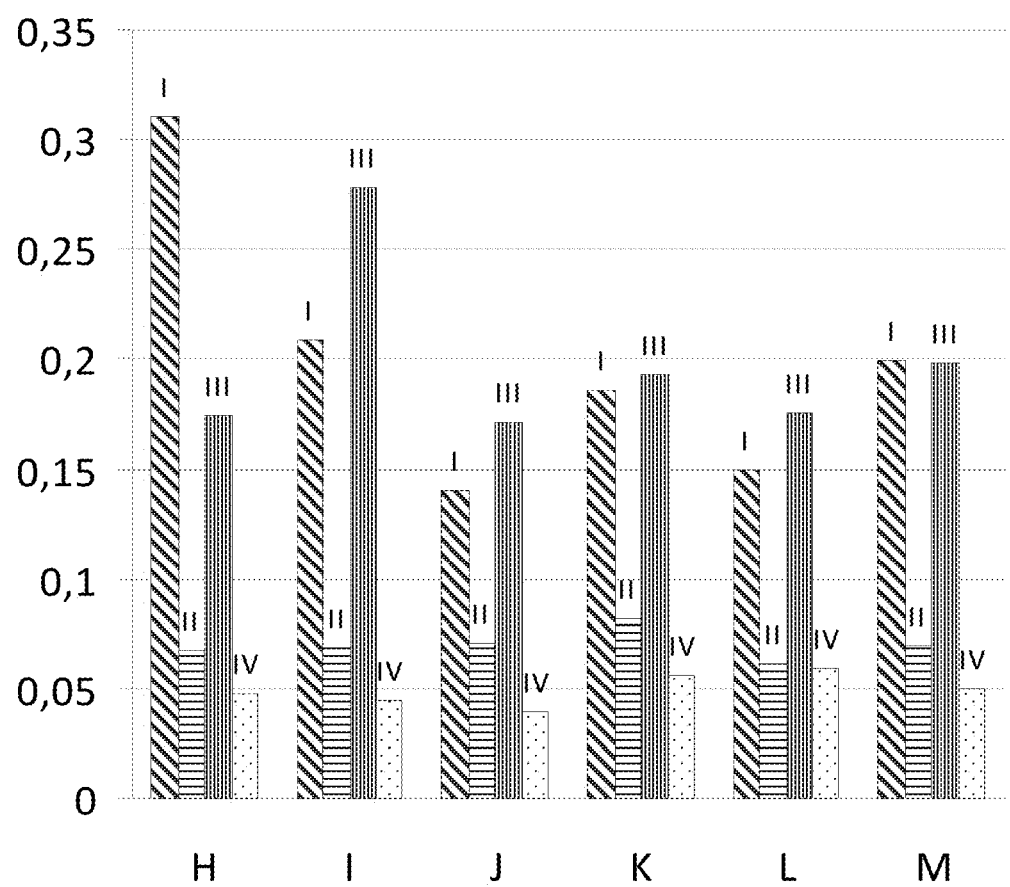
FIG. 11 shows RMS/Amplitude RS in mid-speed (H), fast-speed (I), torso-move (J), racket (K), jump (L), and all the activities, mid-speed, fast-speed, torso move, racket and jump (M) for ZEPHYR™ strap (I), Polar strap (II), NUMETREX® shirt (III) and the shirt of the invention (IV).

FIG. 11 depicts RMS/Amplitude RS in mid-speed (H), fast-speed (I), torso-moving (J), racket (K), jumping (L), and all the activities, mid-speed, fast-speed, torso moving, racket and jumping (M) for ZEPHYR™ HxM strap (I), Polar TEAM² strap (II), NUMETREX® Cardio-Shirt (III) and the shirt of the invention (IV). Based on the results, it is apparent that the shirt of the invention had the best results.

Figure 12:
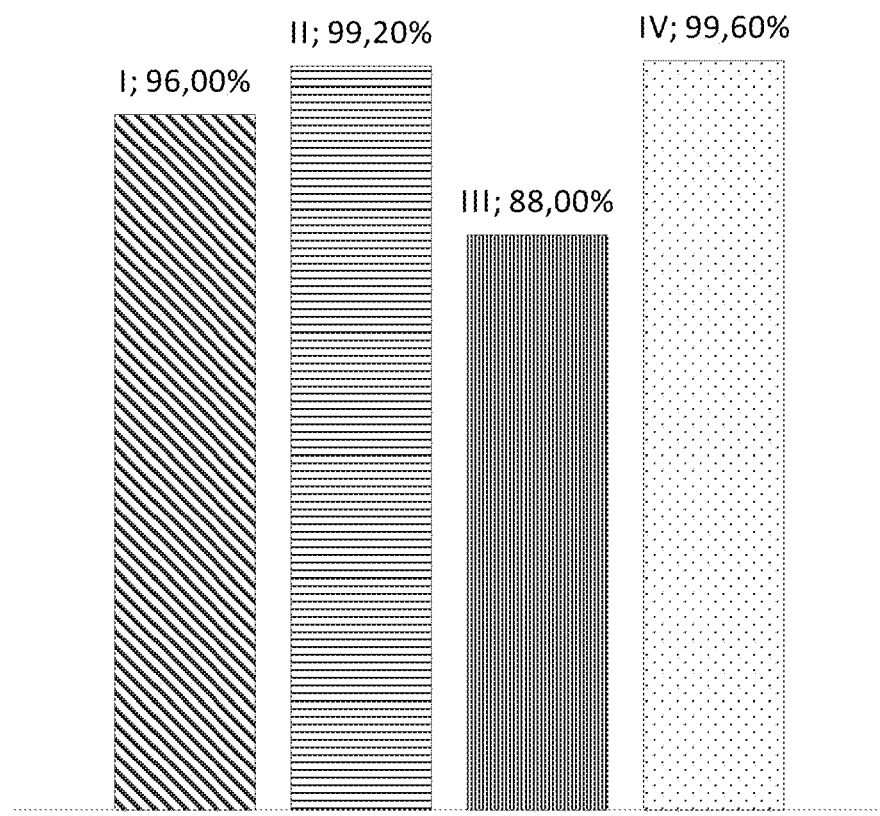
FIG. 12 shows percentage of good QRS complex in strong physical activity for ZEPHYR™ strap (I), Polar strap (II), NUMETREX® shirt (III) and the shirt of the invention (IV).

FIG. 12 depicts the percentage of a good QRS complex during strong physical activity for ZEPHYR™ HxM strap (I), Polar TEAM² strap (II), NUMETREX® Cardio-Shirt (III) and the shirt of the invention (IV). Based on the results of the experiment, the shirt of the invention had the best results.

Figure 13:
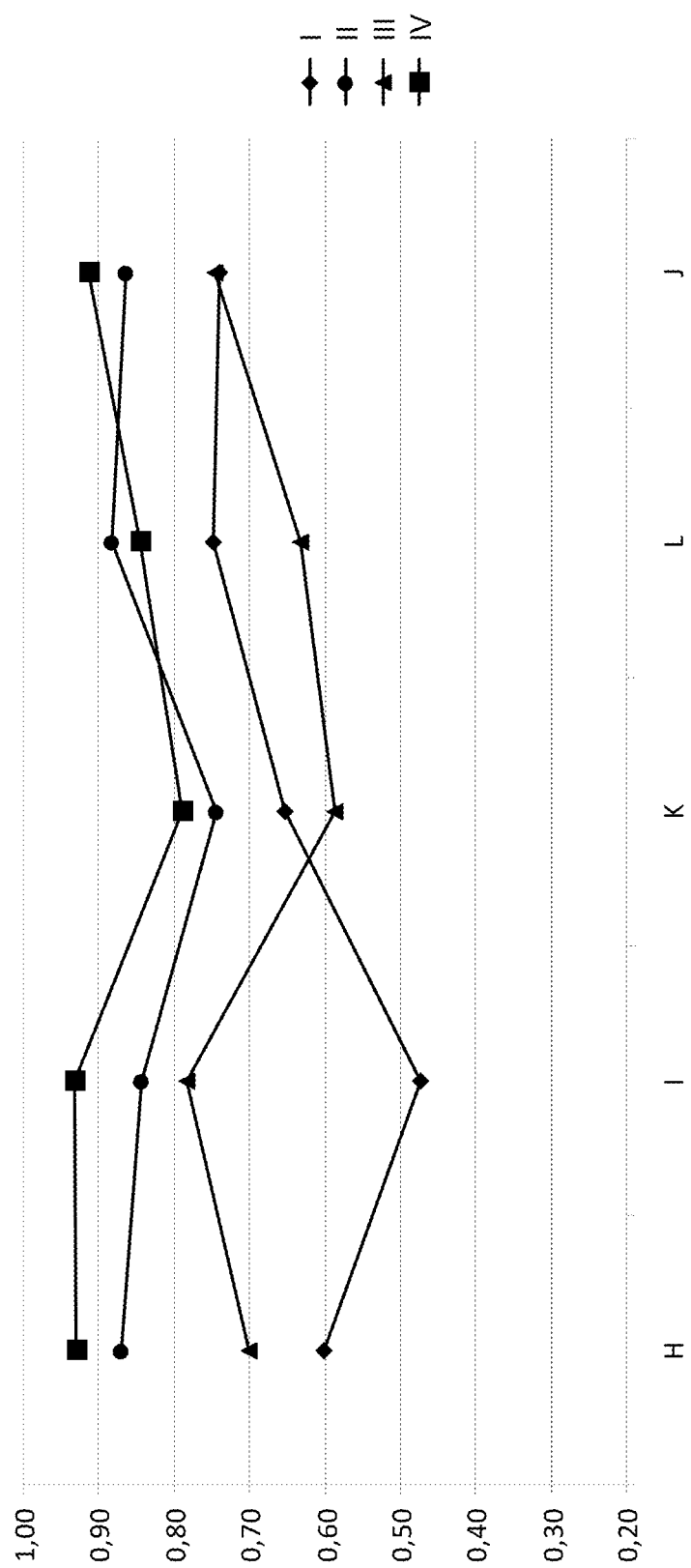
FIG. 13 shows autocorrelation value ZEPHYR™ HxM strap (I), Polar TEAM$^2$ strap (II), NUMETREX® Cardio-Shirt (III) and the shirt of the invention (IV) in mid-speed (H), fast-speed (I), torso-move (J), racket (K) and jump (L).

FIG. 13 depicts the autocorrelation value for ZEPHYR™ HxM strap (I), Polar TEAM² strap (II), NUMETREX® Cardio-Shirt (III) and the shirt of the invention (IV) in mid-speed (H), fast-speed (I), torso-move (J), racket (K) and jump (L). Based on the results, the shirt of the invention had the best results.

Example 2

The experiment involved a shirt of the invention (IV), wherein the track and the electrode are made of conductive fabric and the electrode area has the orifices filled with silicone rubber, and a shirt of the invention without silicone rubber (V). The protocol followed was the same as described above comparing a garment of the invention with other garments by other manufacturers.

Figure 14:
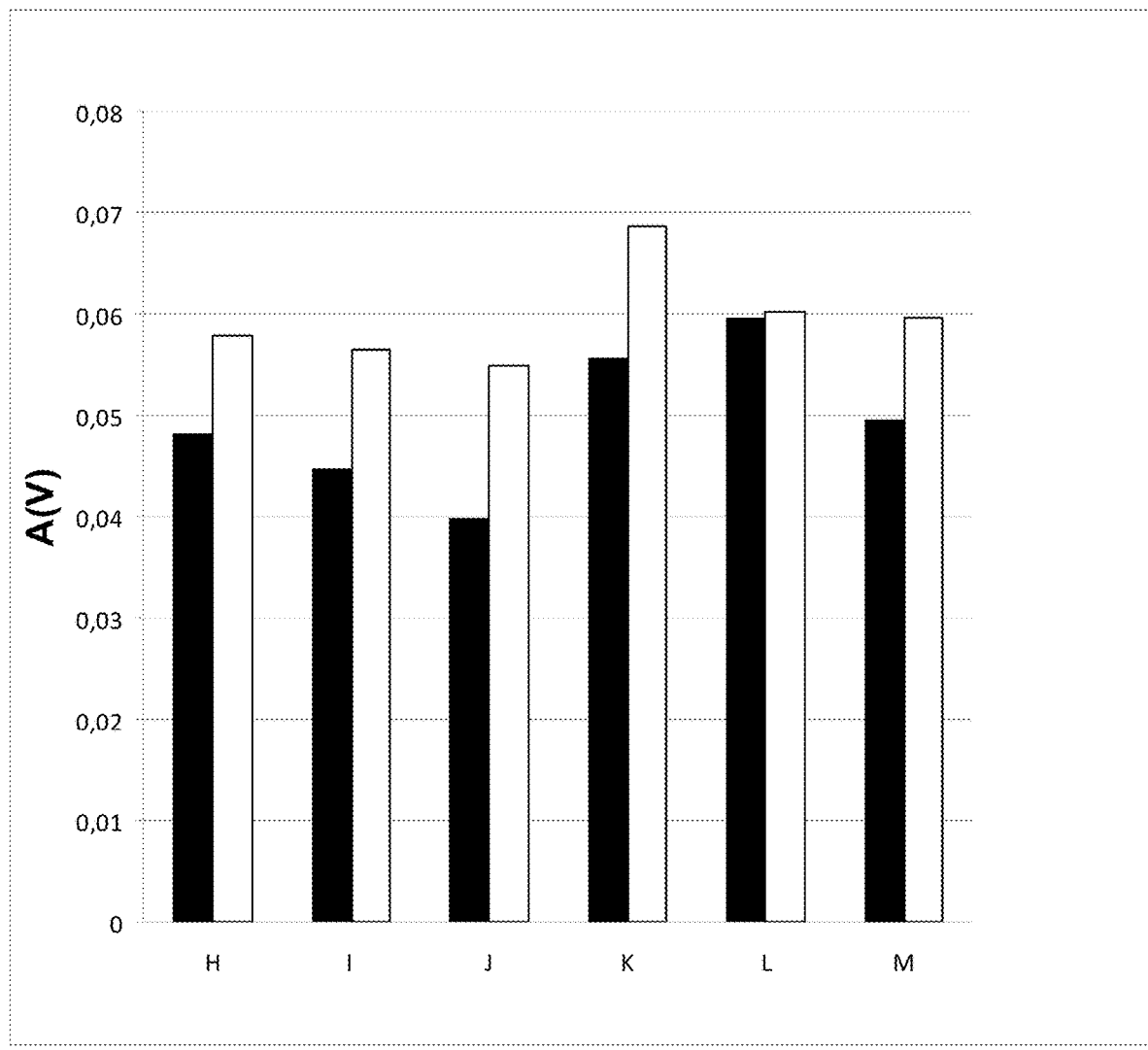
FIG. 14 shows RMS/Amplitude RS in mid-speed (H), fast-speed (I), torso-move (J), racket (K), jump (L), and all the activities, mid-speed, fast-speed, torso move, racket and jump (M) for the shirt of the invention (IV), black column and the shirt of the invention without silicone rubber (V), white column.

FIG. 14 depicts an RMS/Amplitude RS in mid-speed (H), fast-speed (I), torso-moving (J), racket (K), jumping (L), and all the activities, mid-speed, fast-speed, torso moving, racket and jumping (M) for a shirt of the invention (IV) and a shirt of the invention without silicone rubber in the orifices of the electrode area. As depicted, a shirt of the invention with silicone in the orifices of the electrode area had the best results, as seen by the lower noise and better signal. In addition, the shirt with silicone in the electrodes showed better adherence to the skin.

Example 3

In this experiment, the performance of the fabric of the invention was measured at different levels of stretching to evaluate how the stretching affected the quality of the signal. The fabric in the example comprises an electrically conductive area which comprises a conductive silicone (VP97065/30 from Alpina Technische Produkte GmbH), two electrodes of conductive fabric made of conductive fibers and non-conductive fibers, wherein the conductive fibers are made of silver coated nylon (X-Static® yarns from Laird Sauquoit Industries) and non-conductive fibers are made of nylon.

To test and evaluate the signals transmitted through the electrically conductive area (track) comprising conductive silicone VP97065/30, the electrically conductive area was subjected to different levels of stretching. Three states were evaluated: resting, electrically conductive area stretched by about 25% and electrically conductive area stretched by about 50%.

The signal was generated by a PS420 Multiparameter Patient ECG Simulator (from Fluke Corporation) and passed through electrodes, and conducted via the conductive silicone to an electronic instrument for receiving and transmitting the signal to a computer for visualization and further analysis.

For reference, the Resting state of the electrically conductive area where it is not stretched, had a length 6.5 cm. For further reference, 25% Stretching increased the length of the electrically conductive area to 8.125 cm and 50% Stretching increased the length of the electrically conductive area to 9.75 cm. For each state (Resting, 25% and 50% stretching) two segments of signals were captured consisting of 9-10 heart beats of the ECG Simulator (10 seconds each segment because the simulator is configured at 60 beats per minute).

Visual Measures

This measure was determined by watching the signal and evaluating the quality of the signal acquired in terms of morphology and noise detected. This visual recognition is also used to identify what beats (QRS complexes) and characteristic waves were recognizable and which of them are too noisy to be recognized by a cardiologist. A total of 500 beats were analyzed for each different level of electrically conductive area stretching.

Measures Over the Signal

These measures were made on the signal registered in each level of stretching. These measures involve manual and automatic analysis of the recorded signals.

Cross correlation: the signal was separated between the different levels of stretching and compared with the correlation between each other. The cross-correlation was a measure of similarity of two waveforms as a function of a time-lag applied to one of them. This was relevant as it was used an ECG Simulator that generated the same beats with no difference between them. As a result, when a cross-correlation between two signals (one with no stretching and one with stretching) is conducted, the only difference between them will be the noise. This measure goes from 0 (no similarity, completely different) to 1 (the signals are equal).

RMS Noise: the RMS (Root Mean Square) of the T-P segment was be calculated in between heartbeats. This measure was done for each stretching level and averaged. The RMS provides an estimate of the noise in the signal. These measures were done manually (to select the beginning and end of each segment). Both values were very important and very good estimators of the noise present in the signal and the distortion introduced by the stretching of the silicone rubber loaded with electrically conductive material.

Visual Results Obtained Taking Captures of the Signal Directly from the Computer The line that crosses the ECG strips indicates the point where the stretching started and maintained until the end of the strip.

Figure 16:
FIG. 16 shows ECG strip where the electrically conductive area was stretched by about 25% of its original length. Left part of the strip (left of the line), the electrically conductive areas aren't stretched, and the right part of the strip (right of the line) the electrically conductive areas are 25% stretched.
Figure 17:
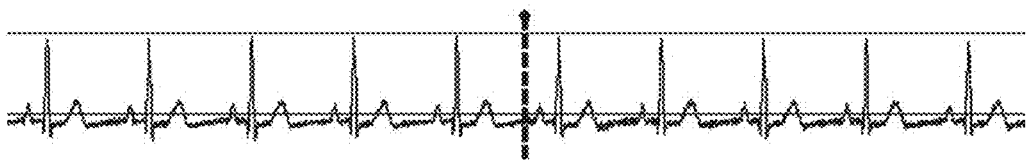
FIG. 17 shows ECG strip where the electrically conductive area was stretched by about 25% of its original length. Left part of the strip (left of the line), the electrically conductive areas aren't stretched, and the right part of the strip (right of the line) the electrically conductive areas are 25% stretched.

25% Streching: Two examples, (FIG. 16, FIG. 17), it is seen that the left part of the strip (left of the line) did not stretch the electrically conductive area, and the right part of the strip (right of the line) did stretch the electrically conductive area.

Figure 18:
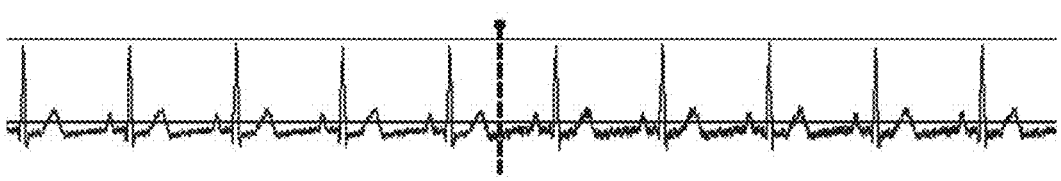
FIG. 18 shows ECG strip where the electrically conductive area was stretched by about 50% of its original length. Left part of the strip (left of the line), the electrically conductive areas aren't stretched, and the right part of the strip (right of the line) the electrically conductive areas are 50% stretched.
Figure 19:
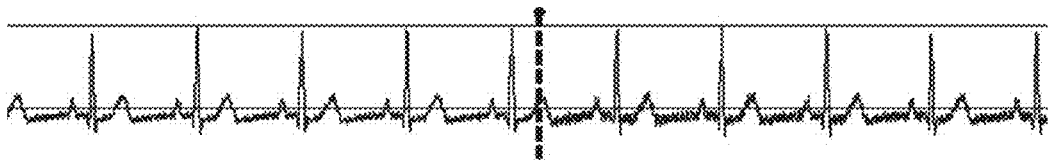
FIG. 19 shows ECG strip where the electrically conductive area was stretched by about 50% of their original length. Left part of the strip (left of the line), the tracks aren't stretched, and the right part of the strip (right of the line) the electrically conductive areas are 50% stretched.

50% Streching: Two examples, (FIG. 18, FIG. 19), it is seen that the left part of the strip (left of the line) did not stretch the electrically conductive area, and the right part of the strip (right of the line) did stretch the electrically conductive area.

As depicted in these figure, it is clear that the quality of the signal was barely affected by the stretching of the electrically conductive area. While more noise was present and visible when the track was stretched to 50%, this noise was not sufficient to corrupt the signal. In addition, the waves and characteristic points were still visible and what noise existed, was easily filtered in a post processing.

Signal Measures Results: RMS Noise

25% Stretching: The results are given for four different segments, two of them with the electrically conductive area not stretched (NO STRETCH_1 and NO STRETCH_2) and the other two with the electrically conductive areas 25% stretched (25% STRETCHING_1 and 25% STRETCHING_2).

TABLE 1

| RMS Noise | |
|---|---|
| | RMS Noise |
| No Stretch 1 | 0.11918993 |
| 25% Streching 1 | 0.13268027 |
| No Stretch 2 | 0.14075932 |
| 25% Streching 2 | 0.14376695 |

In both cases, the signal without stretching the electrically conductive areas had less noise than when the electrically conductive area was stretched after that. This is further found when looking at the average RMS Noise results in Table 2.

TABLE 2

| Average RMS Noise | |
|---|---|
| | RMS Noise |
| No Stretch | 0.12997463 |
| 25% Streching | 0.13822361 |

50% Stretching: The results are given for four different segments, two of them with the electrically conductive area not stretched (NO STRETCH_1 and NO STRETCH_2) and the other two with the electrically conductive area 50% stretched (50% STRETCHING_1 and 50% STRETCHING_2).

TABLE 3

RMS Noise

| | RMS Noise |
|---|---|
| No Stretch 1 | 0.14470239 |
| 50% Streching 1 | 0.14615933 |
| No Stretch 2 | 0.14576144 |
| 50% Streching 2 | 0.15123728 |

In both cases, the signal without stretching the electrically conductive area had less noise than when the electrically conductive area was stretched after that. This is further found when looking at the average RMS Noise results in Table 2.

TABLE 4

Average RMS Noise

| | RMS Noise |
|---|---|
| No Stretch | 0.14523191 |
| 50% Streching | 0.1486983 |

As the difference between the two states was not significant, it is apparent that very little noise was present due to the stretching of the electrically conductive area.

Cross Correlation

Table 5 shows the results for the 25% Stretching and 50% Stretching.

TABLE 5

Cross Correlation

| | Cross Correlation |
|---|---|
| No Stretch/25% Strech | 0.975041781 |
| No Stretch/50% Strech | 0.960290 |

As seen in Table 5, the signal was barely corrupted by noise in either situation. Though the 50% stretching was a little worse than that of the 25% stretching, the difference in the results was not significant as they differed by only 4%.

Example 4

In this example, a comparative test between an elastic semi-conductive track directly in contact with a rigid electrical connector (Assembly 1) and the elastic semi-conductive track and flexible conductive support base assembly of the invention wherein the rigid electrical connector is in contact with the support base (Assembly 2) was conducted.

Assemblies where prepared with elastic semi-conductive track made with the conductive silicone rubber loaded with carbon black, VP97065/30 (Alpina Technische Produkte GmbH); Assembly 2 included a flexible support base which was prepared with a conductive textile made with conductive fibres of silver coated nylon commercialized as X-STATIC® (Laird Sauquoit Industries), and non-conductive fibres of nylon; whereas the substrate in both assemblies was made with polyester, nylon and LYCRA® fibres.

The tracks were 80 mm long and 15 mm wide. Tests were repeated 3 times. Resistivity between both extremes of the track was measured in order to evaluate the durability of the assembly. Resistivity increases with elongations of material, in case of a break the resistivity is drastically increased. Generally, resistency values should not exceed 25 kΩ. Each test consisted of applying three cycles of different lengths of stretching. The first cycle of 30 repetitions subjected specimens to 140% elongation (Table 6).

TABLE 6

| | 100% | 140% |
|---|---|---|
| Assembly 1 | | |
| 001 | 1.7 kΩ | 7 kΩ |
| 002 | 2.2 kΩ | 4.7 kΩ |
| 003 | 1.6 kΩ | 5.8 kΩ |
| Assembly 2 | | |
| 001 | 1.5 kΩ | 2.3 kΩ |
| 002 | 1 kΩ | 1.6 kΩ |
| 003 | 1.5 kΩ | 2.3 kΩ |

In a further experiment, cycle of 30 repetitions subjected specimens to 200% elongation (Table 7).

TABLE 7

| | 100% | 200% |
|---|---|---|
| Assembly 1 | | |
| 001 | 1.7 kΩ | 13.8 kΩ |
| 002 | 2.2 kΩ | 18.2 kΩ |
| 003 | 1.6 kΩ | 10.4 kΩ |
| Assembly 2 | | |
| 001 | 1.5 kΩ | 6.1 kΩ |
| 002 | 1 kΩ | 4.2 kΩ |
| 003 | 1.5 kΩ | 5.9 kΩ |

A third cycle of 5 repetitions subjecting the specimens to 250% elongation (Table 8).

TABLE 8

| | 100% | 250% |
|---|---|---|
| Assembly 1 | | |
| 001 | 1.7 kΩ | 33.2 kΩ |
| 002 | 2.2 kΩ | 930 kΩ (break) |
| 003 | 1.6 kΩ | 29.4 kΩ |
| Assembly 2 | | |
| 001 | 1.5 kΩ | 10.6 kΩ |
| 002 | 1 kΩ | 8.3 kΩ |
| 003 | 1.5 kΩ | 10.1 kΩ |

Aspects of the present specification may also be described as follows:

1. An assembly comprising an elastic semi-conductive or conductive track and a flexible conductive support base assembly arranged on a fabric, the flexible conductive base being a textile comprising conductive fibers and having at least one of its ends shaped, wherein at least one end of the track is in contact with said at least one shaped end of at least one flexible conductive support base, and the non-contact area by the track of the at least one flexible conductive support base is in electrical contact with a rigid electrical component.

2. The assembly of embodiment 1, wherein each end of the track are treading on two different flexible conductive support bases.

3. The assembly of embodiment 2, wherein on the non-treaded area of one of the flexible conductive support bases there is arranged a rigid electrical component, and the non-treaded area of the other flexible conductive support base is adapted to be used as an electrode.

4. The assembly of embodiment 1, wherein the conductive support base is attached to the fabric with an adhesive.

5. The assembly of embodiment 1, wherein the track comprises a layer of silicone rubber and/or fluorosilicone rubber loaded with an electrically conductive material.

6. The assembly of embodiment 1, wherein the track comprises a layer of a room temperature curing silicone rubber and/or fluorsilicone rubber loaded with an electrically conductive material selected from carbon fibres, carbon black, nickel coated graphite, copper fibres and mixtures thereof.

7. The assembly of embodiment 1, wherein the thickness of the elastic and electrically conductive track comprising a thickness of at least 25 µm, 50 µm, 75 µm, 100 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, 300 µm, 325 µm, 350 µm, 375 µm, 400 µm, 425 µm, 450 µm, 475 µm, 500 µm, 525 µm, 550 µm, 575 µm, 600 µm, 625 µm, 650 µm, 675 µm, 700 µm, 725 µm, 750 µm, 775 µm, 800 µm, 825 µm, 850 µm, 875 µm, 900 µm, 925 µm, 950 µm, 975 µm, 1000 µm.

8. The assembly of embodiment 5, wherein the track is integrated into the textile fabric substrate and partially into the at least one shaped end of the conductive support base by anchoring the silicone with the structure of the fibres of the textile fabric substrate and the conductive support base when cured the silicone at room temperature after being screen-printed on them.

9. The assembly of embodiment 1, wherein the silicone rubber and/or flourosilicone rubber is screen-printed on a fabric and on the at least one round shaped end of the conductive support base applying a pressure comprising at least 0.1 Kg/m$^2$, at least 0.2 Kg/m$^2$, at least 0.3 Kg/m$^2$, at least 0.4 Kg/m$^2$, at least 0.5 Kg/m$^2$, at least 0.6 Kg/m$^2$, at least 0.7 Kg/m$^2$, at least 0.8 Kg/m$^2$, at least 0.9 Kg/m$^2$, at least 1 Kg/m$^2$.

10. The assembly according of embodiment 1, wherein the cured temperature of the silicone rubber and/or fluorosilicone rubber loaded with an electrically conductive material is of from 20° C. to 200° C., of from 50° C. to 140° C. or of from 100° C. to 120° C.

11. The assembly according of embodiment 1, wherein the cured temperature of the silicone rubber and/or fluorosilicone rubber loaded with an electrically conductive material is no more than 5° C., no more than 10° C., no more than 15° C., no more than 20° C., no more than 25° C., no more than 30° C., no more than 35° C., no more than 40° C., no more than 45° C., no more than 50° C., no more than 55° C., no more than 60° C., no more than 65° C., no more than 70° C., no more than 75° C., no more than 80° C., no more than 85° C., no more than 90° C., no more than 95° C., no more than 100° C., no more than 110° C., no more than 120° C., no more than 130° C., no more than 140° C., no more than 150° C., no more than 160° C., no more than 165, no more than 170° C., no more than 180° C., no more than 190° C., no more than 200° C., no more than 210° C., no more than 220° C., no more than 230° C., no more than 240° C., no more than 250° C., no more than 260° C., no more than 270° C., no more than 280° C., no more than 290° C. or no more than 300° C.

12. A sensor adapted to be incorporated in a garment, said sensor comprising an assembly of embodiment 3, wherein the electrode is adapted to obtain physiological signals through its contact with the skin of the wearer of the garment.

13. The sensor of embodiment 12, wherein a track is electrically isolated from its contact with the skin of the wearer of the garment, and a rigid electrical component is an electrical connector adapted to transmit a physiological signal obtained through the electrode to an electronic instrument.

14. The sensor of embodiment 12, wherein the electrode comprises a conductive fabric made of conductive fibers and non-conductive fibers.

15. The sensor of embodiment 12, wherein the electrode is characterized in that the conductive layer comprises a plurality of orificies filled with an silicone rubber throughout the conductive area.

16. A device comprising the sensor as defined in embodiment 12, and an electronic instrument for receiving, collecting, storing, processing and/or transmitting data from said sensor.

17. A garment comprising the device of embodiment 16.

18. A method for monitoring a physiological signal of a user comprising receiving, collecting, storing, processing and/or transmitting one or more parameters indicative of at least one physiological signal of a user originating from at least one sensor as defined in embodiment 13 incorporated in a garment; and evaluating said physiological signal along the time.

19. The method of embodiment 18, wherein the physiological signal is an ECG signal.

20. A sensor which comprises an electrode, a track and an electrical connector, wherein, the track is comprising an electrically conductive flexible and elastic material that comprises an electrically conductive material that is non-continguous that when stretched is able to transmit a signal from an electrode to an electrical connector and from an electrical connector to an electrode.

21. The sensor of embodiment 20, wherein an electrically conductive flexible and elastic material is constructed of silicone rubber and/or fluorosilicone rubber and an electrically conductive material.

22. The sensor of embodiment 21, wherein the silicone rubber and/or fluorosilicone rubber is loaded with an amount comprising no more than 1% w/w, 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w, 15% w/w, 16% w/w, 17% w/w, 18% w/w, 19% w/w, 20% w/w, 21% w/w, 22% w/w, 23% w/w, 24% w/w, 26% w/w, 27% w/w, 28% w/w, 29% w/w, 30% w/w, 31% w/w, 32% w/w, 33% w/w, 34% w/w, 35% w/w, 36% w/w, 37% w/w, 38% w/w, 39% w/w, 40% w/w, 41% w/w, 42% w/w, 43% w/w, 44% w/w, 45% w/w, 46% w/w, 47% w/w, 48% w/w, 49% w/w, 50% w/w, 51% w/w, 52% w/w, 53% w/w, 54% w/w, 55% w/w, 56% w/w, 57% w/w, 58% w/w, 59% w/w, 60% w/w, 65% w/w, 70% w/w, 75% w/w, 80% w/w, 85% w/w, 90% w/w, 95% w/w or more of an electrically conductive material.

23. The sensor of embodiment 22, wherein the electrically conductive material is selected from the group of carbon fibers, carbon black, nickel coated graphite, copper fibres or a metal powder.

24. The sensor of embodiment 23, wherein the carbon black is selected from furnace black, lamp black, thermal black, acetylene black, channel black.

25. The sensor of embodiment 23, wherein the metal powder is selected from silver, nickel, and copper.

26. The sensor of embodiment 21, wherein a resistance value, from one end of a sensor, to the other is less than 50 KΩ, 100 KΩ, 150 KΩ, 200 KΩ, 250 KΩ, 300 KΩ, 350 KΩ, 400 KΩ, 450 KΩ, 500 KΩ, 550 KΩ, 600 KΩ, 650 KΩ, 700 KΩ, 750 KΩ, 800 KΩ, 850 KΩ, 900 KΩ, 950 KΩ or 100 KΩ when the flexible material is stretched.

27. The sensor of embodiment 21, wherein the sensor is able to stretch at least 1%, at least 2%, at least 3%, at least 4%, at least 5%, 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% at least 100%, at least 105%, at least 110%, at least 115%, at least 120%, at least 125%, at least 130%, at least 135%, at least 140%, at least 145%, at least 150%, at least 155%, at least 160%, at least 165%, at least 170%, at least 175%, at least 180%, at least 185%, at least 190%, at least 195%, at least 200%, at least 210%, at least 220%, at least 230%, at least 240%, at least 250%, at least 260%, at least 270%, at least 280%, at least 290%, at least 300% or more as compared to the same sensor when it is not stretched.

28. The sensor of embodiment 22, wherein the silicone rubber is cured at a temperature of no more than 5° C., no more than 10° C., no more than 15° C., no more than 20° C., no more than 25° C., no more than 30° C., no more than 35° C., no more than 40° C., no more than 45° C., no more than 50° C., no more than 55° C., no more than 60° C., no more than 65° C., no more than 70° C., no more than 75° C., no more than 80° C., no more than 85° C., no more than 90° C., no more than 95° C., no more than 100° C., no more than 110° C., no more than 120° C., no more than 130° C., no more than 140° C., no more than 150° C., no more than 160° C., no more than 165, no more than 170° C., no more than 180° C., no more than 190° C., no more than 200° C., no more than 210° C., no more than 220° C., no more than 230° C., no more than 240° C., no more than 250° C., no more than 260° C., no more than 270° C., no more than 280° C., no more than 290° C. or no more than 300° C.

29. The sensor of embodiment 22, wherein the silicone rubber and/or fluorosilicone rubber is liquid printed.

30. The sensor of embodiment 22, wherein the silicone rubber and/or fluorosilicone rubber is screen printed.

31. The sensor of embodiment 22, wherein the silicone rubber and/or fluorosilicone rubber has a molecular weight of at least 100 g/mol, 200 g/mol, 300 g/mol, 325 g/mol, 350 g/mol, 375 g/mol, 400 g/mol, 425 g/mol, 450 g/mol, 475 g/mol, 500 g/mol, 525 g/mol, 550 g/mol, 575 g/mol, 600 g/mol, 625 g/mol, 650 g/mol, 674 g/mol, 700 g/mol, 800 g/mol, 900 g/mol, 1000 g/mol, or more.

32. The sensor of embodiment 22, wherein the silicone rubber and/or fluorosilicone rubber has a molecular weight of no more than 100 g/mol, 200 g/mol, 300 g/mol, 325 g/mol, 350 g/mol, 375 g/mol, 400 g/mol, 425 g/mol, 450 g/mol, 475 g/mol, 500 g/mol, 525 g/mol, 550 g/mol, 575 g/mol, 600 g/mol, 625 g/mol, 650 g/mol, 674 g/mol, 700 g/mol, 800 g/mol, 900 g/mol or 1000 g/mol.

33. The sensor of embodiment 21, wherein the electrode is characterized in that the conductive layer comprises a plurality of orificies filled with an silicone rubber throughout the conductive area.

34. The sensor of embodiment 21, wherein the resistance of the electrode is at least 0.5Ω, at least 1Ω, at least 2Ω, at least, 3Ω, at least 4Ω, at least 5Ω, at least 6Ω, at least 7Ω, at least 8Ω, at least 9Ω, at least 10Ω, at least 11Ω, at least 12Ω, at least 13Ω, at least 14Ω, or at least 15Ω or more.

35. The sensor of embodiment 21, wherein the track is integrated into the textile fabric substrate and partially into the at least one round shaped end of the conductive support base by anchoring the silicone with the structure of the fibers of the textile fabric substrate and the conductive support base.

36. The sensor of embodiment 21, where in at least an elastic and electrically conductive track integrated into the fabric, and wherein the elastic and electrically conductive track comprises a silicone rubber and/or fluorosilicone rubber loaded with an electrically conductive material, wherein the thickness of the elastic and electrically conductive track is at least 25 µm, 50 µm, 75 µm, 100 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, 300 µm, 325 µm, 350 µm, 375 µm, 400 µm, 425 µm, 450 µm, 475 µm, 500 µm, 525 µm, 550 µm, 575 µm, 600 µm, 625 µm, 650 µm, 675 µm, 700 µm, 725 µm, 750 µm, 775 µm, 800 µm, 825 µm, 850 µm, 875 µm, 900 µm, 925 µm, 950 µm, 975 µm, or 1000 µm.

37. The sensor of embodiment 21, wherein the resistance of the track is at least 1Ω, at least 2Ω, at least, 3Ω, at least 4Ω, at least 5Ω, at least 6Ω, at least 7Ω, at least 8Ω, at least 9Ω, at least 10Ω, at least 11Ω, at least 12Ω, at least 13Ω, at least 14Ω, at least 15Ω, at least 16Ω, at least 17Ω, at least 18Ω, at least 19Ω, at least 20Ω, at least 21Ω, at least 22Ω, at least 23Ω, at least 24Ω, at least 25Ω, at least 26Ω, at least 27Ω, at least 28Ω, at least 29Ω, at least 30Ω, at least 31Ω, at least 32Ω, at least 33Ω, at least 34Ω, at least 35Ω, at least 36Ω, at least 37Ω, at least 38Ω, at least 39Ω, at least 40Ω, at least 41Ω, at least 42Ω, at least 43Ω, at least 44Ω, at least 45Ω, at least 46Ω, at least 47Ω, at least 48Ω, at least 49Ω, at least 50Ω, or more.

38. The sensor of embodiment 21, wherein a track is electrically isolated from its contact with the skin of the wearer of the garment, and a rigid electrical component is an electrical connector adapted to transmit a physiological signal obtained through the electrode to an electronic instrument.

39. The sensor of embodiment 21, wherein the sensor is able to detect physiological signals.

40. The sensor of embodiment 39, wherein the physiological signals detected are cardiac pulse, respiratory frequency, electrodermal response (EDR), measurement of electrical skin conductivity, electrocardiography (ECG), temperature, skin impedance, transpiration and electromyography (EMG).

41. A fabric which comprises a sensor, wherein the sensor includes an electrode, a track and an electrical connector, wherein, an elastic semi-conductive or conductive track and a flexible conductive support base assembly arranged on a fabric substrate, the flexible conductive base being a textile comprising conductive and non-conductive fibers and having at least one of its ends round shaped, wherein at least one end of the track is treading on said at least one end round shaped of at least one flexible conductive support base, and the non-treaded area by the track of the at least one flexible conductive support base is in electrical contact with a rigid electrical component.

42. A process for the preparation of a fabric as defined in embodiment 41, which comprises the steps of: a) liquid-printing a first layer of silicone rubber and/or fluorosilicone rubber loaded with an amount between 5% w/w to 40% w/w of an electrically conductive material into the fabric; b) pre-curing the first layer for up one minute at a temperature between 80° C. to 200° C.; c) curing the first layer at room temperature.

43. The process of embodiment 42, wherein the liquid-printing step comprises applying a pressure comprising at least 0.1 Kg/m$^2$, at least 0.2 Kg/m$^2$, at least 0.3 Kg/m$^2$, at least 0.4 Kg/m$^2$, at least 0.5 Kg/m$^2$, at least 0.6 Kg/m$^2$, at least 0.7 Kg/m$^2$, at least 0.8 Kg/m$^2$, at least 0.9 Kg/m$^2$, at least 1 Kg/m$^2$ when printing the silicone rubber and/or fluorosilicone rubber loaded with the electrically conductive material directly to the fabric.

44. A physiological signal fabric adapted to be incorporated in a garment, said fabric comprising the sensor as defined in embodiment 21, wherein the electrode is adapted to obtain physiological signals through its contact with the skin of the wearer of the garment.

45. A device comprising the sensor as defined in embodiment 21, and an electronic instrument for receiving, collecting, storing, processing and/or transmitting data from said sensor.

46. A garment comprising the device of embodiment 45.

47. A method for monitoring a physiological signal of a user comprising receiving, collecting, storing, processing and/or transmitting one or more parameters indicative of at least one physiological signal of a user originating from at least one sensor as defined in embodiment 21 incorporated in a garment; and evaluating said physiological signal along the time.

48. The sensor of embodiment 20, wherein the resistance of the electrode is at least 0.5Ω, at least 1Ω, at least 2Ω, at least, 3Ω, at least 4Ω, at least 5Ω, at least 6Ω, at least 7Ω, at least 8Ω, at least 9Ω, at least 10Ω, at least 11Ω, at least 12Ω, at least 13Ω, at least 14Ω, at least 15Ω or more.

49. The sensor of embodiment 20, wherein the sensor is able to detect physiological signals.

50. The sensor of embodiment 49, wherein the physiological signals detected are cardiac pulse, respiratory frequency, electrodermal response (EDR), measurement of electrical skin conductivity, electrocardiography (ECG), temperature, skin impedance, transpiration and electromyography (EMG).

51. A fabric which comprises a sensor, wherein the sensor includes an electrode, a track and an electrical connector, wherein, the track is comprising an electrically conductive flexible material that is non-continguous that when stretched is able to transmit a signal from an electrode to an electrical connector and from an electrical connector to an electrode that when stretched is able to transmit a signal from an electrode to an electrical connector and from an electrical connector to an electrode.

52. The fabric of embodiment 51, wherein an electrically conductive flexible material is constructed of silicone rubber and/or fluorosilicone rubber and an electrically conductive material.

53. The fabric of embodiment 52, wherein the electrically conductive material is selected from the group of carbon fibers, carbon black, nickel coated graphite, copper fibres or a metal powder.

54. The fabric of embodiment 53, wherein the carbon black is selected from furnace black, lamp black, thermal black, acetylene black, channel black.

55. The fabric of embodiment 53, wherein the metal powder is selected from silver, nickel, and copper.

56. The fabric of embodiment 51, wherein a resistance value, from one end of a sensor, to the other is less than 50 KΩ, 100 KΩ, 150 KΩ, 200 KΩ, 250 KΩ, 300 KΩ, 350 KΩ, 400 KΩ, 450 KΩ, 500 KΩ, 550 KΩ, 600 KΩ, 650 KΩ, 700 KΩ, 750 KΩ, 800 KΩ, 850 KΩ, 900 KΩ, 950 KΩ or 1000 KΩ when the flexible material is stretched.

57. The fabric of embodiment 52, wherein the silicone rubber is cured at a temperature of no more than 5° C., no more than 10° C., no more than 15° C., no more than 20° C., no more than 25° C., no more than 30° C., no more than 35° C., no more than 40° C., no more than 45° C., no more than 50° C., no more than 55° C., no more than 60° C., no more than 65° C., no more than 70° C., no more than 75° C., no more than 80° C., no more than 85° C., no more than 90° C., no more than 95° C., no more than 100° C., no more than 110° C., no more than 120° C., no more than 130° C., no more than 140° C., no more than 150° C., no more than 160° C., no more than 165, no more than 170° C., no more than 180° C., no more than 190° C., no more than 200° C., no more than 210° C., no more than 220° C., no more than 230° C., no more than 240° C., no more than 250° C., no more than 260° C., no more than 270° C., no more than 280° C., no more than 290° C. or no more than 300° C.

58. The fabric of embodiment 52, wherein the silicone rubber and/or fluorosilicone rubber is liquid printed.

59. The fabric of embodiment 52, wherein the silicone rubber and/or fluorosilicone rubber is screen printed.

60. The fabric of embodiment 52, wherein the silicone rubber and/or fluorosilicone rubber has a molecular weight of at least 100 g/mol, 200 g/mol, 300 g/mol, 325 g/mol, 350 g/mol, 375 g/mol, 400 g/mol, 425 g/mol, 450 g/mol, 475 g/mol, 500 g/mol, 525 g/mol, 550 g/mol, 575 g/mol, 600 g/mol, 625 g/mol, 650 g/mol, 674 g/mol, 700 g/mol, 800 g/mol, 900 g/mol, 1000 g/mol, or more.

61. The fabric of embodiment 52, wherein the silicone rubber and/or fluorosilicone rubber has a molecular weight of no more than 100 g/mol, 200 g/mol, 300 g/mol, 325 g/mol, 350 g/mol, 375 g/mol, 400 g/mol, 425 g/mol, 450 g/mol, 475 g/mol, 500 g/mol, 525 g/mol, 550 g/mol, 575 g/mol, 600 g/mol, 625 g/mol, 650 g/mol, 674 g/mol, 700 g/mol, 800 g/mol, 900 g/mol or 1000 g/mol.

62. The fabric of embodiment 51, wherein the resistance of the electrode is at least 0.5Ω, at least 1Ω, at least 2Ω, at least, 3Ω, at least 4Ω, at least 5Ω, at least 6Ω, at least 7Ω, at least 8Ω, at least 9Ω, at least 10Ω, at least 11Ω, at least 12Ω, at least 13Ω, at least 14Ω, at least 15Ω or more.

63. The sensor of embodiment 16, wherein the resistance of the track is at least 1Ω, at least 2Ω, at least, 3Ω, at least 4Ω, at least 5Ω, at least 6Ω, at least 7Ω, at least 8Ω, at least 9Ω, at least 10Ω, at least 11Ω, at least 12Ω, at least 13Ω, at least 14Ω, at least 15Ω, at least 16Ω, at least 17Ω, at least 18Ω, at least 19Ω, at least 20Ω, at least 21Ω, at least 22Ω, at least 23Ω, at least 24Ω, at least 25Ω, at least 26Ω, at least 27Ω, at least 28Ω, at least 29Ω, at least 30Ω, at least 31Ω, at least 32Ω, at least 33Ω, at least 34Ω, at least 35Ω, at least 36Ω, at least 37Ω, at least 38Ω, at least 39Ω, at least 40Ω, at least 41Ω, at least 42Ω, at least 43Ω, at least 44Ω, at least 45Ω, at least 46Ω, at least 47Ω, at least 48Ω, at least 49Ω, at least 50Ω, or more.

64. The fabric of embodiment 51, wherein the sensor is able to detect physiological signals.

65. The fabric of embodiment 64, wherein the physiological signals detected are cardiac pulse, respiratory frequency, electrodermal response (EDR), measurement of electrical skin conductivity, electrocardiography (ECG), temperature, skin impedance, transpiration and electromyography (EMG).

66. The fabric of embodiment 51, which further comprises a layer of an insulating material covering the track.

67. The fabric of embodiment 51, wherein the fabric comprises an electrode to be placed in contact with the skin of a user.

68. The fabric of embodiment 51, wherein the electrode comprises a conductive fabric made of conductive fibers and non-conductive fibers.

69. The fabric of embodiment 52, wherein the electrode comprises a layer of silicone rubber and/or fluorosilicone rubber loaded with an amount comprising at least 1% w/w, 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w, 15% w/w, 16% w/w, 17% w/w, 18% w/w, 19% w/w, 20% w/w, 21% w/w, 22% w/w, 23% w/w, 24% w/w, 26% w/w, 27% w/w, 28% w/w, 29% w/w, 30% w/w, 31% w/w, 32% w/w, 33% w/w, 34% w/w, 35% w/w, 36% w/w, 37% w/w, 38% w/w, 39% w/w, 40% w/w, 41% w/w, 42% w/w, 43% w/w, 44% w/w, 45% w/w, 46% w/w, 47% w/w, 48% w/w, 49% w/w, 50% w/w, 51% w/w, 52% w/w, 53% w/w, 54% w/w, 55% w/w, 56% w/w, 57% w/w, 58% w/w, 59% w/w, 60% w/w, 65% w/w, 70% w/w, 75% w/w, 80% w/w, 85% w/w, 90% w/w, 95% w/w or more of an electrically conductive material.

70. The fabric of embodiment 52, wherein the silicone rubber and/or fluorosilicone rubber is loaded with an amount comprising no more than 1% w/w, 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w, 15% w/w, 16% w/w, 17% w/w, 18% w/w, 19% w/w, 20% w/w, 21% w/w, 22% w/w, 23% w/w, 24% w/w, 26% w/w, 27% w/w, 28% w/w, 29% w/w, 30% w/w, 31% w/w, 32% w/w, 33% w/w, 34% w/w, 35% w/w, 36% w/w, 37% w/w, 38% w/w, 39% w/w, 40% w/w, 41% w/w, 42% w/w, 43% w/w, 44% w/w, 45% w/w, 46% w/w, 47% w/w, 48% w/w, 49% w/w, 50% w/w, 51% w/w, 52% w/w, 53% w/w, 54% w/w, 55% w/w, 56% w/w, 57% w/w, 58% w/w, 59% w/w, 60% w/w, 65% w/w, 70% w/w, 75% w/w, 80% w/w, 85% w/w, 90% w/w, 95% w/w or more of an electrically material.

71. The fabric of embodiment 51, wherein the fabric is able to stretch at least 1%, at least 2%, at least 3%, at least 4%, at least 5%, 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 105%, at least 110%, at least 115%, at least 120%, at least 125%, at least 130%, at least 135%, at least 140%, at least 145%, at least 150%, at least 155%, at least 160%, at least 165%, at least 170%, at least 175%, at least 180%, at least 185%, at least 190%, at least 195%, at least 200%, at least 210%, at least 220%, at least 230%, at least 240%, at least 250%, at least 260%, at least 270%, at least 280%, at least 290%, at least 300% or more as compared to the same fabric when it is not stretched.

72. The fabric of embodiment 51, wherein at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the electrode and track are in contact with the skin on an individual.

73. The fabric of embodiment 51, wherein no more than 5%, no more than 10%, no more than 15%, no more than 20%, no more than 25%, no more than 30%, no more than 35%, no more than 40%, no more than 45%, no more than 50%, no more than 55%, no more than 60%, no more than 65%, no more than 70%, no more than 75%, no more than 80%, no more than 85%, no more than 90%, no more than 95%, or no more than 100% of the electrode and track are in contact with the skin of an individual.

74. The fabric of embodiment 51, wherein the proportion of a flexible semi-conductive or conductive material in contact with the skin of an individual is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the total conductive layer.

75. The fabric of embodiment 51, the proportion of a flexible semi-conductive or conductive material to be in contact with the skin of an individual is no more than 5%, no more than 10%, no more than 15%, no more than 20%, no more than 25%, no more than 30%, no more than 35%, no more than 40%, no more than 45%, no more than 50%, no more than 55%, no more than 60%, no more than 65%, no more than 70%, no more than 75%, no more than 80%, no more than 85%, no more than 90%, no more than 95%, or no more than 100% of the electrode and track are in contact with the skin of an individual.

76. The fabric of embodiment 51, wherein an electrically conductive material is loaded with an amount comprising from 5% w/w to 40% w/w comprising: a) diorganopolysiloxane gum having silicon-bonded alkenyl groups; b) organohydrogenpolysiloxanes; c) a platinum catalyst; and d) between 5-40% w/w of an electrically conductive material.

77. A process for the preparation of a fabric as defined in embodiment 51, which comprises the steps of: a) liquid-printing a first layer of silicone rubber loaded with an amount between 5% w/w to 40% w/w of a electrically conductive material into the fabric; b) pre-curing the first layer for up one minute at a temperature between 80° C. to 200° C.; c) curing the first layer at room temperature.

78. The process according to embodiment 77, wherein the liquid-printing step comprises applying a pressure comprising from 0.2 to 0.8 Kg/m$^2$ when printing the silicone rubber loaded with the electrically conductive material directly to the fabric.

79. The process according to embodiment 77, wherein the liquid-printing step comprises applying a pressure comprising from 0.3 to 0.5 Kg/m$^2$ when printing the silicone rubber loaded with the electrically conductive material directly to the fabric.

80. A device comprising: a) the fabric as defined in embodiment 51; and b) an electronic instrument for receiving and collecting and/or storing and/or processing, and/or transmitting data from said fabric.

81. A garment comprising the device of embodiment 80.

82. A device comprising the sensor as defined in embodiment 51, and an electronic instrument for receiving, collecting, storing, processing and/or transmitting data from said sensor.

83. A garment comprising the device of embodiment 82.

84. A method for monitoring a physiological signal of a user comprising receiving, collecting, storing, processing and/or transmitting one or more parameters indicative of at least one physiological signal of a user originating from at least one sensor as defined in embodiment 51 incorporated in a garment; and evaluating said physiological signal along the time.

85. The method of embodiment 84, wherein the physiological signal is an ECG signal.

86. A fabric which comprises at least an elastic and electrically conductive track integrated into the fabric, and wherein the elastic and electrically conductive track comprises a silicone rubber and/or fluorosilicone rubber loaded with an electrically conductive material, wherein the thickness of the elastic and electrically conductive track comprising from 120 to 800 μm thick, from 120-500 μm thick, from 250-500 μm thick or from 300-400 μm thick.

87. The fabric of embodiment 86, wherein the electrically conductive material is screen printed with a thickness of at least 25 μm, 50 μm, 75 μm, 100 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm, 290 μm, 300 μm, 325 μm, 350 μm, 375 μm, 400 μm, 425 μm, 450 μm, 475 μm, 500 μm, 525 μm, 550 μm, 575 μm, 600 μm, 625 μm, 650 μm, 675 μm, 700 μm, 725 μm, 750 μm, 775 μm, 800 μm, 825 μm, 850 μm, 875 μm, 900 μm, 925 μm, 950 μm, 975 μm, 1000 μm.

88. The fabric of embodiment 86, wherein the electrically conductive material is screen printed with a thickness of no more than 25 μm, 50 μm, 75 μm, 100 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm, 290 μm, 300 μm, 325 μm, 350 μm, 375 μm, 400 μm, 425 μm, 450 μm, 475 μm, 500 μm, 525 μm, 550 μm, 575 μm, 600 μm, 625 μm, 650 μm, 675 μm, 700 μm, 725 μm, 750 μm, 775 μm, 800 μm, 825 μm, 850 μm, 875 μm, 900 μm, 925 μm, 950 μm, 975 μm, 1000 μm.

89. The fabric of embodiment 86, which further comprises a layer of an insulating material covering the track, wherein the insulating material may or may not include an electrically conductive material.

90. The fabric of embodiment 86, wherein the fabric comprises an electrode to be placed in contact with the skin of an user and in electrical contact with a flexible and electrically conductive track.

91. The fabric of embodiment 90, wherein the electrode comprises a conductive fabric made of conductive fibers and non-conductive fibers.

92. The fabric of embodiment 90, wherein the electrode comprises a layer of silicone rubber loaded with an amount between 5% w/w to 40% w/w of an elastic and electrically conductive material, which is integrated into the fabric.

93. The fabric of embodiment 90, wherein the electrode comprises a layer of silicone rubber, loaded with an amount comprising at least 1% w/w, 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w, 15% w/w, 16% w/w, 17% w/w, 18% w/w, 19% w/w, 20% w/w, 21% w/w, 22% w/w, 23% w/w, 24% w/w, 26% w/w, 27% w/w, 28% w/w, 29% w/w, 30% w/w, 31% w/w, 32% w/w, 33% w/w, 34% w/w, 35% w/w, 36% w/w, 37% w/w, 38% w/w, 39% w/w, 40% w/w, 41% w/w, 42% w/w, 43% w/w, 44% w/w, 45% w/w, 46% w/w, 47% w/w, 48% w/w, 49% w/w, 50% w/w, 51% w/w, 52% w/w, 53% w/w, 54% w/w, 55% w/w, 56% w/w, 57% w/w, 58% w/w, 59% w/w, 60% w/w, 65% w/w, 70% w/w, 75% w/w, 80% w/w, 85% w/w, 90% w/w, 95% w/w or more of an electrically conductive material.

94. The fabric of embodiment 90, wherein the electrode comprises a layer of silicone rubber, loaded with an amount comprising an amount of no more than 1% w/w, 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w, 15% w/w, 16% w/w, 17% w/w, 18% w/w, 19% w/w, 20% w/w, 21% w/w, 22% w/w, 23% w/w, 24% w/w, 26% w/w, 27% w/w, 28% w/w, 29% w/w, 30% w/w, 31% w/w, 32% w/w, 33% w/w, 34% w/w, 35% w/w, 36% w/w, 37% w/w, 38% w/w, 39% w/w, 40% w/w, 41% w/w, 42% w/w, 43% w/w, 44% w/w, 45% w/w, 46% w/w, 47% w/w, 48% w/w, 49% w/w, 50% w/w, 51% w/w, 52% w/w, 53% w/w, 54% w/w, 55% w/w, 56% w/w, 57% w/w, 58% w/w, 59% w/w, 60% w/w, 65% w/w, 70% w/w, 75% w/w, 80% w/w, 85% w/w, 90% w/w, 95% w/w or more of an electrically conductive material.

95. The fabric of embodiment 86, wherein the electrical resistance per cm of a flexible material loaded with an electrically conductive material is comprising from 50 Ω/cm to 100 kΩ/cm.

96. The fabric of embodiment 86, wherein the electrical resistance per cm of a flexible material, loaded with an electrically conductive material is less than 1 KΩ/cm, less than 2 KΩ/cm, less than 3 KΩ/cm, less than 4 KΩ/cm, less than 5 KΩ/cm, less than 6 KΩ/cm, less than 7 KΩ/cm, less than 8 KΩ/cm, less than 9 KΩ/cm, less than 10 KΩ/cm, less than 11 KΩ/cm, less than 12 KΩ/cm, less than 13 KΩ/cm, less than 14 KΩ/cm, less than 15 KΩ/cm, less than 16 KΩ/cm, less than 17 KΩ/cm, less than 18 KΩ/cm, less than 19 KΩ/cm, less than 20 KΩ/cm, less than 21 KΩ/cm, less than 22 KΩ/cm, less than 23 KΩ/cm, less than 24 KΩ/cm, less than 25 KΩ/cm, less than 26 KΩ/cm, less than 27 KΩ/cm, less than 28 KΩ/cm, less than 29 KΩ/cm, less than 30 KΩ/cm, less than 31 KΩ/cm, less than 32 KΩ/cm, less than 33 KΩ/cm, less than 34 KΩ/cm, less than 35 KΩ/cm, less than 36 KΩ/cm, less than 37 KΩ/cm, less than 38 KΩ/cm, less than 39 KΩ/cm, less than 40 KΩ/cm, less than 41 KΩ/cm, less than 42 KΩ/cm, less than 43 KΩ/cm, less than 44 KΩ/cm, less than 45 KΩ/cm, less than 46 KΩ/cm, less than 47 KΩ/cm, less than 48 KΩ/cm, less than 49 KΩ/cm, less than 50 KΩ/cm, 55 KΩ/cm, less than 60 KΩ/cm, less than 65 KΩ/cm, less than 70 KΩ/cm, less than 75 KΩ/cm, less than 80 KΩ/cm, less than 85 KΩ/cm, less than 90 KΩ/cm, less than 95 KΩ/cm, less than 100 KΩ/cm, 150 KΩ/cm, 200 KΩ/cm, 250 KΩ/cm, 300 KΩ/cm, 350 KΩ/cm, 400 KΩ/cm, 450 KΩ/cm, 500 KΩ/cm, 550 KΩ/cm, 600 KΩ/cm, 650 KΩ/cm, 700 KΩ/cm, 750 KΩ/cm, 800 KΩ/cm, 850 KΩ/cm, 900 KΩ/cm, 950 KΩ/cm or 100 KΩ/cm.

97. The fabric according of embodiment 86, wherein the cured temperature of the silicone rubber and/or fluorosilicone rubber loaded with an electrically conductive material is of from 20° C. to 200° C., of from 50° C. to 140° C. or of from 100° C. to 120° C.

98. The fabric according of embodiment 86, wherein the cured temperature of the silicone rubber and/or fluorosilicone rubber loaded with an electrically conductive material is no more than 5° C., no more than 10° C., no more than 15° C., no more than 20° C., no more than 25° C., no more than 30° C., no more than 35° C., no more than 40° C., no more than 45° C., no more than 50° C., no more than 55° C., no more than 60° C., no more than 65° C., no more than 70° C., no more than 75° C., no more than 80° C., no more than 85° C., no more than 90° C., no more than 95° C., no more than 100° C., no more than 110° C., no more than 120° C., no more than 130° C., no more than 140° C., no more than 150° C., no more than 160° C., no more than 165, no more than 170° C., no more than 180° C., no more than 190° C., no more than 200° C., no more than 210° C., no more than 220° C., no more than 230° C., no more than 240° C., no more than 250° C., no more than 260° C., no more than 270° C., no more than 280° C., no more than 290° C. or no more than 300.

99. The fabric of embodiment 86, wherein the silicone rubber and/or fluorosilicoe rubber loaded with an amount comprising from 5% w/w to 40% w/w of a electrically conductive material comprises: a) diorganopolysiloxane gum having silicon-bonded alkenyl groups; b) organohydrogenpolysiloxanes; c) a platinum catalyst; and d) between 5-40% w/w of an electrically conductive material.

100. The fabric of embodiment 86, wherein the electrically conductive material is carbon fibers, carbon black, nickel coated graphite, copper fibers and mixtures thereof or various metal powders such as silver, nickel, and copper.

101. The fabric of embodiment 100, wherein the carbon black is furnace black, lamp black, thermal black, acetylene black, channel black.

102. A process for the preparation of a fabric as defined in embodiment 86, which comprises the steps of: a) liquid-printing a first layer of silicone rubber and/or fluorosilicone rubber loaded with an amount between 5% w/w to 40% w/w of an electrically conductive material into the fabric; b) pre-curing the first layer for up one minute at a temperature between 80° C. to 200° C.; c) curing the first layer at room temperature.

103. The process of embodiment 102, wherein the liquid-printing step comprises applying a pressure comprising from 0.2 to 0.8 Kg/m$^2$, from 0.3 to 0.5 Kg/m$^2$; or from 0.45 Kg/m$^2$ when printing the silicone rubber and/or fluorsilicone rubber loaded with the electrically conductive material directly to the fabric.

104. The process of embodiment 102, wherein the liquid-printing step comprises applying a pressure comprising at least 0.1 Kg/m$^2$, at least 0.2 Kg/m$^2$, at least 0.3 Kg/m$^2$, at least 0.4 Kg/m$^2$, at least 0.5 Kg/m$^2$, at least 0.6 Kg/m$^2$, at least 0.7 Kg/m$^2$, at least 0.8 Kg/m$^2$, at least 0.9 Kg/m$^2$, at least 1 when printing the silicone rubber and/or fluorosilicone rubber loaded with the electrically conductive material directly to the fabric.

105. Use of a silicone rubber and/or fluorosilicone rubber loaded with an amount comprising from 5% w/w to 40% w/w of an electrically conductive material for the preparation of the fabric of embodiment 86.

106. The use of a silicone rubber and/or fluorsilicone rubber of embodiment 102, wherein the silicone rubber and/or fluorosilicone rubber is comprising no more than 1% w/w, 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w, 15% w/w, 16% w/w, 17% w/w, 18% w/w, 19% w/w, 20% w/w, 21% w/w, 22% w/w, 23% w/w, 24% w/w, 26% w/w, 27% w/w, 28% w/w, 29% w/w, 30% w/w, 31% w/w, 32% w/w, 33% w/w, 34% w/w, 35% w/w, 36% w/w, 37% w/w, 38% w/w, 39% w/w, 40% w/w, 41% w/w, 42% w/w, 43% w/w, 44% w/w, 45% w/w, 46% w/w, 47% w/w, 48% w/w, 49% w/w, 50% w/w, 51% w/w, 52% w/w, 53% w/w, 54% w/w, 55% w/w, 56% w/w, 57% w/w, 58% w/w, 59% w/w, 60% w/w, 65% w/w, 70% w/w, 75% w/w, 80% w/w, 85% w/w, 90% w/w, 95% w/w or more of an electrically conductive material.

107. A device comprising: a) the fabric as defined in embodiment 86, b) an electronic instrument for receiving and collecting and/or storing and/or processing, and/or transmitting data from said fabric.

108. A garment comprising a device of embodiment 107.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A fabric which comprises a sensor, wherein the sensor includes an elastic conductive track, a rigid electrical component, and a flexible conductive support base arranged on a textile fabric substrate, the flexible conductive support base being a conductive fabric comprising interlaced conductive fibers and non-conductive fibers and a plurality of orifices throughout a conductive area of the flexible conductive support base, and having at least one of its ends round shaped, wherein at least one end of the track is in contact with the at least one round shaped end of the flexible conductive support base, and a non-contacted area of the flexible conductive support base is in electrical contact with the rigid electrical component, wherein the plurality of orifices are filled with a silicone rubber, and wherein the silicone rubber is attached to the conductive fabric without use of an adhesive.

2. The fabric of claim 1, wherein the elastic conductive track is constructed of silicone rubber and/or fluorosilicone rubber and an electrically conductive material.

3. The fabric of claim 2, wherein the silicone rubber and/or fluorosilicone rubber is loaded with an amount comprising no more than 1% w/w, 2% w/w, 3% w/w, 4% w/w, 5% w/w, 6% w/w, 7% w/w, 8% w/w, 9% w/w, 10% w/w, 11% w/w, 12% w/w, 13% w/w, 14% w/w, 15% w/w, 16% w/w, 17% w/w, 18% w/w, 19% w/w, 20% w/w, 21% w/w, 22% w/w, 23% w/w, 24% w/w, 26% w/w, 27% w/w, 28% w/w, 29% w/w, 30% w/w, 31% w/w, 32% w/w, 33% w/w, 34% w/w, 35% w/w, 36% w/w, 37% w/w, 38% w/w, 39% w/w, 40% w/w, 41% w/w, 42% w/w, 43% w/w, 44% w/w, 45% w/w, 46% w/w, 47% w/w, 48% w/w, 49% w/w, 50% w/w, 51% w/w, 52% w/w, 53% w/w, 54% w/w, 55% w/w, 56% w/w, 57% w/w, 58% w/w, 59% w/w, 60% w/w, 65% w/w, 70% w/w, 75% w/w, 80% w/w, 85% w/w, 90% w/w, 95% w/w or more of an electrically conductive material.

4. The fabric of claim 3, wherein the electrically conductive material is selected from the group of carbon fibers, carbon black, nickel coated graphite, copper fibres or a metal powder.

5. The fabric of claim 4, wherein the carbon black is selected from furnace black, lamp black, thermal black, acetylene black, and channel black.

6. The fabric of claim 4, wherein the metal powder is selected from silver, nickel, and copper.

7. The fabric of claim 2, wherein a resistance value, from one end of the sensor to an opposing end of the sensor is less than 50 K$\Omega$, 100 K$\Omega$, 150 K$\Omega$, 200 K$\Omega$, 250 K$\Omega$, 300 K$\Omega$, 350 K$\Omega$, 400 K$\Omega$, 450 K$\Omega$, 500 K$\Omega$, 550 K$\Omega$, 600 K$\Omega$, 650 K$\Omega$, 700 K$\Omega$, 750 K$\Omega$, 800 K$\Omega$, 850 K$\Omega$, 900 K$\Omega$, 950 K$\Omega$ or 100 K$\Omega$ when the electrically conductive material is stretched.

8. The fabric of claim 2, wherein the sensor is able to stretch at least 1%, at least 2%, at least 3%, at least 4%, at least 5%, 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% at least 100%, at least 105%, at least 110%, at least 115%, at least 120%, at least 125%, at least 130%, at least 135%, at least 140%, at least 145%, at least 150%, at least 155%, at least 160%, at least 165%, at least 170%, at least 175%, at least 180%, at least 185%, at least 190%, at least 195%, at least 200%, at least 210%, at least 220%, at least 230%, at least 240%, at least 250%, at least 260%, at least 270%, at least 280%, at least 290%, at least 300% or more as compared to the same sensor when it is not stretched.

9. The fabric of claim 3, wherein the silicone rubber is cured at a temperature of no more than 5° C., no more than 10° C., no more than 15° C., no more than 20° C., no more than 25° C., no more than 30° C., no more than 35° C., no more than 40° C., no more than 45° C., no more than 50° C., no more than 55° C., no more than 60° C., no more than 65° C., no more than 70° C., no more than 75° C., no more than 80° C., no more than 85° C., no more than 90° C., no more than 95° C., no more than 100° C., no more than 110° C., no more than 120° C., no more than 130° C., no more than 140° C., no more than 150° C., no more than 160° C., no more than 165, no more than 170° C., no more than 180° C., no more than 190° C., no more than 200° C., no more than 210° C., no more than 220° C., no more than 230° C., no more than 240° C., no more than 250° C., no more than 260° C., no more than 270° C., no more than 280° C., no more than 290° C. or no more than 300° C.

10. The fabric of claim 3, wherein the silicone rubber and/or fluorosilicone rubber is liquid printed.

11. The fabric of claim 3, wherein the silicone rubber and/or fluorosilicone rubber is screen printed.

12. The fabric of claim 3, wherein the silicone rubber and/or fluorosilicone rubber has a molecular weight of at least 100 g/mol, 200 g/mol, 300 g/mol, 325 g/mol, 350 g/mol, 375 g/mol, 400 g/mol, 425 g/mol, 450 g/mol, 475 g/mol, 500 g/mol, 525 g/mol, 550 g/mol, 575 g/mol, 600 g/mol, 625 g/mol, 650 g/mol, 674 g/mol, 700 g/mol, 800 g/mol, 900 g/mol, 1000 g/mol, or more.

13. The fabric of claim 3, wherein the silicone rubber and/or fluorosilicone rubber has a molecular weight of no more than 100 g/mol, 200 g/mol, 300 g/mol, 325 g/mol, 350 g/mol, 375 g/mol, 400 g/mol, 425 g/mol, 450 g/mol, 475 g/mol, 500 g/mol, 525 g/mol, 550 g/mol, 575 g/mol, 600 g/mol, 625 g/mol, 650 g/mol, 674 g/mol, 700 g/mol, 800 g/mol, 900 g/mol or 1000 g/mol.

14. The fabric of claim 2, wherein the resistance of the flexible conductive support base is at least 0.50, at least 1$\Omega$, at least 2$\Omega$, at least, 3$\Omega$, at least 4$\Omega$, at least 5$\Omega$, at least 6$\Omega$, at least 7$\Omega$, at least 8$\Omega$, at least 9$\Omega$, at least 10$\Omega$, at least 11$\Omega$, at least 12$\Omega$, at least 13$\Omega$, at least 14$\Omega$, at least 15$\Omega$ or more.

15. The fabric of claim 2, wherein the elastic conductive track is integrated into the textile fabric substrate and partially into the at least one round shaped end of the conductive support base by anchoring the silicone with the structure of the fibers of the textile fabric substrate and the conductive support base.

16. The fabric of claim 2, wherein a thickness of the elastic conductive track is at least 25 µm, 50 µm, 75 µm, 100 µm, 120 µm, 130 µm, 140 µm, 150 µm, 160 µm, 170 µm, 180 µm, 190 µm, 200 µm, 210 µm, 220 µm, 230 µm, 240 µm, 250 µm, 260 µm, 270 µm, 280 µm, 290 µm, 300 µm, 325 µm, 350 µm, 375 µm, 400 µm, 425 µm, 450 µm, 475 µm, 500 µm, 525 µm, 550 µm, 575 µm, 600 µm, 625 µm, 650 µm, 675 µm, 700 µm, 725 µm, 750 µm, 775 µm, 800 µm, 825 µm, 850 µm, 875 µm, 900 µm, 925 µm, 950 µm, 975 µm, 1000 µm.

17. The fabric of claim 2, wherein the resistance of the elastic conductive track is at least 1$\Omega$, at least 2$\Omega$, at least, 3$\Omega$, at least 4$\Omega$, at least 5$\Omega$, at least 6$\Omega$, at least 7$\Omega$, at least 8$\Omega$, at least 9$\Omega$, at least 10$\Omega$, at least 11$\Omega$, at least 12$\Omega$, at least 13$\Omega$, at least 14$\Omega$, at least 15$\Omega$, at least 16$\Omega$, at least 17$\Omega$, at least 18$\Omega$, at least 19$\Omega$, at least 20$\Omega$, at least 21$\Omega$, at least 22$\Omega$, at least 23$\Omega$, at least 24$\Omega$, at least 25$\Omega$, at least 26$\Omega$, at least 27$\Omega$, at least 28$\Omega$, at least 29$\Omega$, at least 30$\Omega$, at least 31$\Omega$, at least 32$\Omega$, at least 33$\Omega$, at least 34$\Omega$, at least 35$\Omega$, at least 36$\Omega$, at least 37$\Omega$, at least 38$\Omega$, at least 39$\Omega$, at least 40$\Omega$, at least 41$\Omega$, at least 42$\Omega$, at least 43$\Omega$, at least 44$\Omega$, at least 45$\Omega$, at least 46$\Omega$, at least 47$\Omega$, at least 48$\Omega$, at least 49$\Omega$, at least 50$\Omega$, or more.

18. The fabric of claim 2, wherein the elastic conductive track is electrically isolated from its contact with the skin of the wearer of the garment, and the rigid electrical component is an electrical connector adapted to transmit a physiological signal obtained through the flexible conductive support base to an electronic instrument.

19. A process for preparinq the fabric as defined in claim 1, which comprises the steps of:
liquid-printing a first layer of silicone rubber and/or fluorosilicone rubber loaded with an amount between 5% w/w to 40% w/w of an electrically conductive material into the fabric;
pre-curing the first layer for up one minute at a temperature between 80° C. to 200° C.; and
curing the first layer at room temperature.

20. The process of claim 19, wherein the liquid-printing step comprises applying a pressure comprising at least 0.1 Kg/m$^2$, at least 0.2 Kg/m$^2$, at least 0.3 Kg/m$^2$, at least 0.4 Kg/m$^2$, at least 0.5 Kg/m$^2$, at least 0.6 Kg/m$^2$, at least 0.7 Kg/m$^2$, at least 0.8 Kg/m$^2$, at least 0.9 Kg/m$^2$, at least 1 Kg/m$^2$ when printing the silicone rubber and/or fluorosilicone rubber loaded with the electrically conductive material directly to the fabric.

\* \* \* \* \*